US008815257B2

(12) United States Patent
Braksmayer et al.

(10) Patent No.: US 8,815,257 B2
(45) Date of Patent: Aug. 26, 2014

(54) COMPOSITIONS COMPRISING METATHESIZED UNSATURATED POLYOL ESTERS

(75) Inventors: Diza Pearl Braksmayer, Chanhassen, MN (US); Timothy A. Murphy, Derby, KS (US); Stephen E. Russell, Grayslake, IL (US); Michael John Tupy, Crystal, MN (US); Scott A. Walters, Sugar Grove, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 654 days.

(21) Appl. No.: 12/281,938

(22) PCT Filed: Mar. 7, 2007

(86) PCT No.: PCT/US2007/005736
§ 371 (c)(1),
(2), (4) Date: Dec. 11, 2008

(87) PCT Pub. No.: WO2007/103398
PCT Pub. Date: Sep. 13, 2007

(65) Prior Publication Data
US 2009/0220443 A1    Sep. 3, 2009

Related U.S. Application Data

(60) Provisional application No. 60/780,125, filed on Mar. 7, 2006.

(51) Int. Cl.
*A61K 9/00* (2006.01)
(52) U.S. Cl.
USPC ............................ 424/400; 424/401; 424/757
(58) Field of Classification Search
None
See application file for complete search history.

(56) References Cited

U.S. PATENT DOCUMENTS

| | | | |
|---|---|---|---|
| 2,619,422 A | 11/1952 | Whiting | |
| 3,448,178 A | 6/1969 | Flanagan | |
| 3,896,053 A | 7/1975 | Broecker et al. | |
| 4,545,941 A * | 10/1985 | Rosenburg | 554/163 |
| 4,634,606 A | 1/1987 | Skogg | |
| 5,043,485 A | 8/1991 | Fleckenstein et al. | |
| 5,142,072 A | 8/1992 | Stipp et al. | |
| 5,506,363 A | 4/1996 | Grate et al. | |
| 5,639,526 A | 6/1997 | Kotsiopoulos et al. | |
| 5,700,516 A | 12/1997 | Sandvick et al. | |
| 5,734,070 A | 3/1998 | Tacke et al. | |
| 5,958,851 A | 9/1999 | Cannon et al. | |
| 6,063,144 A | 5/2000 | Calzada et al. | |
| 6,169,198 B1 | 1/2001 | Fischer et al. | |
| 6,197,894 B1 | 3/2001 | Sunaga et al. | |
| 6,211,315 B1 | 4/2001 | Larock et al. | |
| 6,214,918 B1 | 4/2001 | Johnson et al. | |
| 6,224,641 B1 | 5/2001 | Matzat et al. | |
| 6,255,375 B1 | 7/2001 | Michelman | |
| 6,262,153 B1 | 7/2001 | Webster et al. | |
| 6,281,163 B1 | 8/2001 | Van Dijk | |
| 6,284,007 B1 | 9/2001 | Tao | |
| 6,342,094 B1 * | 1/2002 | Kabalnov | 106/31.25 |
| 6,486,264 B1 | 11/2002 | Tsunogae et al. | |
| 6,503,285 B1 | 1/2003 | Murphy | |
| 6,530,962 B1 | 3/2003 | Stolz | |
| 6,586,506 B2 | 7/2003 | Webster et al. | |
| 6,599,334 B1 | 7/2003 | Anderson | |
| 6,645,261 B2 | 11/2003 | Murphy et al. | |
| 6,696,597 B2 | 2/2004 | Pederson et al. | |
| 6,716,155 B2 | 4/2004 | Sleeter | |
| 6,730,137 B2 | 5/2004 | Pesu et al. | |
| 6,770,104 B2 | 8/2004 | Murphy | |
| 6,773,469 B2 | 8/2004 | Murphy | |
| 6,797,020 B2 | 9/2004 | Murphy | |
| 6,824,572 B2 | 11/2004 | Murphy | |
| 6,846,573 B2 | 1/2005 | Seydel | |
| 6,900,347 B2 | 5/2005 | Paulson et al. | |
| 6,962,729 B2 | 11/2005 | Tokas et al. | |
| 6,987,154 B2 | 1/2006 | Choi et al. | |
| 7,026,495 B1 | 4/2006 | Pedersen et al. | |
| 7,037,439 B2 | 5/2006 | Tavares | |
| 7,119,216 B2 | 10/2006 | Newman et al. | |
| 7,128,766 B2 | 10/2006 | Murphy et al. | |
| 7,176,336 B2 | 2/2007 | Maughon et al. | |
| 7,192,457 B2 | 3/2007 | Murphy et al. | |
| 7,217,301 B2 | 5/2007 | Murphy et al. | |
| 7,314,904 B2 | 1/2008 | Nadolsky et al. | |
| 7,365,140 B2 | 4/2008 | Piers et al. | |

(Continued)

FOREIGN PATENT DOCUMENTS

DE    19956226    5/2001
EP    0429995 A2    6/1991

(Continued)

OTHER PUBLICATIONS

Refvik, M.D. et al., "The Chemistry of Metathesized Soybean Oil," JAOCS, vol. 76, No. 1, 1999, pp. 99-102.
Office Action from counterpart Chinese Application No. 200780016574.6, dated Jan. 26, 2011, 16 pages.
Office Action from co-pending U.S. Appl. No. 12/281,931, dated Feb. 1, 2010, 10 pages.
Patel et al., "High conversion and productive catalyst turnovers in cross-metathesis reactions of natural oils with 2-butene", Green Chemistry, 2006, vol. 8, pp. 450-454.
Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.
Baumann et al., "Natural Fats and Oils—Renewable Raw Materials for the Chemical Industry," Angewandte Chemie International Edition in English, vol. 27, 1988, pp. 41-62.

(Continued)

*Primary Examiner* — James Rogers
(74) *Attorney, Agent, or Firm* — Brinks Gilson & Lione

(57) ABSTRACT

Disclosed are petrolatum-like compositions that comprise metathesized unsaturated polyol esters. Also disclosed are emulsions comprising metathesized unsaturated polyol esters. The petrolatum-like compositions may be used as substitutes for petroleum-based petrolatum. The emulsions may be water-in-oil or oil-in-water emulsions and may be suitable for a variety of end uses.

15 Claims, 9 Drawing Sheets

(56) References Cited

U.S. PATENT DOCUMENTS

| | | |
|---|---|---|
| 7,462,205 B2 | 12/2008 | Murphy |
| 7,576,227 B2 | 8/2009 | Lysenko |
| 7,585,990 B2 | 9/2009 | van Toor et al. |
| 7,678,932 B2 | 3/2010 | Thurier et al. |
| 7,812,185 B2 | 10/2010 | Burdett et al. |
| 2001/0051680 A1 | 12/2001 | Webster et al. |
| 2002/0095007 A1 | 7/2002 | Larock et al. |
| 2002/0157303 A1 | 10/2002 | Murphy et al. |
| 2003/0017431 A1 | 1/2003 | Murphy |
| 2003/0046860 A1 | 3/2003 | Tiffany et al. |
| 2003/0057599 A1 | 3/2003 | Murphy et al. |
| 2003/0061760 A1 | 4/2003 | Tao et al. |
| 2003/0091949 A1 | 5/2003 | Pesu et al. |
| 2003/0110683 A1 | 6/2003 | Murphy |
| 2003/0198826 A1 | 10/2003 | Seydel |
| 2003/0207971 A1 | 11/2003 | Stuart, Jr. et al. |
| 2003/0236377 A1 | 12/2003 | Choi et al. |
| 2004/0047886 A1 | 3/2004 | Murphy et al. |
| 2004/0088907 A1 | 5/2004 | Murphy |
| 2004/0088908 A1 | 5/2004 | Murphy |
| 2004/0200136 A1 | 10/2004 | Tao et al. |
| 2004/0221503 A1 | 11/2004 | Murphy et al. |
| 2004/0221504 A1 | 11/2004 | Murphy |
| 2005/0014664 A1 | 1/2005 | Nadolsky et al. |
| 2005/0027136 A1 | 2/2005 | Toor et al. |
| 2005/0060927 A1 | 3/2005 | Murphy |
| 2005/0070750 A1 | 3/2005 | Newman et al. |
| 2005/0080301 A1 | 4/2005 | Maughon et al. |
| 2005/0123780 A1 | 6/2005 | Seydel |
| 2005/0154221 A1 | 7/2005 | Lysenko et al. |
| 2005/0158679 A1 | 7/2005 | Chen et al. |
| 2005/0269728 A1 | 12/2005 | Roos |
| 2006/0079704 A1 | 4/2006 | Lacombe et al. |
| 2006/0128912 A1 | 6/2006 | Piers et al. |
| 2006/0236593 A1 | 10/2006 | Cap |
| 2006/0272199 A1 | 12/2006 | Licciardello et al. |
| 2006/0272200 A1 | 12/2006 | Murphy et al. |
| 2006/0289138 A1* | 12/2006 | Borsinger et al. ............ 162/172 |
| 2007/0006522 A1 | 1/2007 | Tao |
| 2007/0039237 A1 | 2/2007 | Murphy et al. |
| 2007/0144058 A1 | 6/2007 | Chen et al. |
| 2007/0151480 A1 | 7/2007 | Bloom et al. |
| 2007/0179307 A1 | 8/2007 | Olivier-Bourbigou et al. |
| 2007/0270621 A1 | 11/2007 | Millis et al. |
| 2007/0282000 A1 | 12/2007 | Murphy et al. |
| 2008/0027194 A1 | 1/2008 | Schrodi |
| 2008/0064891 A1 | 3/2008 | Lee |
| 2009/0048459 A1 | 2/2009 | Tupy et al. |
| 2009/0126602 A1 | 5/2009 | Murphy et al. |
| 2009/0217568 A1 | 9/2009 | Murphy et al. |
| 2009/0259065 A1 | 10/2009 | Abraham et al. |
| 2009/0264672 A1 | 10/2009 | Abraham et al. |
| 2010/0047499 A1 | 2/2010 | Braksmayer et al. |
| 2010/0094034 A1 | 4/2010 | Kaido et al. |
| 2010/0145086 A1 | 6/2010 | Schrodi et al. |

FOREIGN PATENT DOCUMENTS

| | | |
|---|---|---|
| EP | 1408064 A1 | 4/2004 |
| FR | 2878246 A1 | 5/2006 |
| JP | 56077243 | 6/1981 |
| JP | 09014574 | 1/1997 |
| SU | 1565872 | 5/1990 |
| WO | WO 94/23836 A1 | 10/1994 |
| WO | WO 96/04289 | 2/1996 |
| WO | WO 00/46565 | 8/2000 |
| WO | WO 01/36368 | 5/2001 |
| WO | WO 01/36368 A2 | 5/2001 |
| WO | WO 03/018905 | 3/2003 |
| WO | WO 03/057983 | 7/2003 |
| WO | WO 03/093215 | 11/2003 |
| WO | WO 03/104348 | 12/2003 |
| WO | WO 2004/033388 | 4/2004 |
| WO | WO 2004/062763 | 7/2004 |
| WO | WO 2004/083310 | 9/2004 |
| WO | WO 2005/026106 | 3/2005 |
| WO | WO 2005/042655 | 5/2005 |
| WO | WO 2005/080455 | 9/2005 |
| WO | WO 2006/052688 | 5/2006 |
| WO | WO 2006/076364 | 7/2006 |
| WO | WO 2007/002999 | 1/2007 |
| WO | WO 2007/081987 | 7/2007 |
| WO | WO 2007/103398 | 9/2007 |
| WO | WO 2007/103460 A2 | 9/2007 |
| WO | WO 2008/008420 A1 | 1/2008 |
| WO | WO 2008/010961 A2 | 1/2008 |
| WO | WO 2008/048520 A2 | 4/2008 |
| WO | WO 2008/063322 A2 | 5/2008 |
| WO | WO 2008/140468 A2 | 11/2008 |

OTHER PUBLICATIONS

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al., "Drying Properties of Metathesized Soybean Oil," Journal of American Oil Chemists' Society, AOCS Press, vol. 74, No. 6, 1997, pp. 703-706.

Feuge et al., "1,3-Diolein and 1,3-Distearin Esters of Fumaric, Succinic and Adipic Acids," Journal of American Chemical Society, vol. 80, 1958, pp. 6338-6341.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Refvik et al., "Ruthenium-Catalyzed Metathesis of Vegetable Oils," Journal of American Oil Chemists' Society, AOCS Press, vol. 76, No. 1, 1999, pp. 93-98.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Shorland, "Glycol Esters of Dibasic Acids. The Di-β-hydroxyethyl Esters," Journal of American Chemical Society, vol. 57, No. 1, 1935, pp. 115-116.

Tian et al., "Model Studies and the ADMET Polymerization of Soybean Oil," Journal of American Oil Chemists' Society, AOCS Press, vol. 79, No. 5, 2002, pp. 479-488.

Ward et al., "New Fat Products: Glyceride Esters of Adipic Acid," Journal of the Amierican Oil Chemists' Society, vol. 36, 1959, pp. 667-671.

International Search Report and Written Opinion of the International Searching Authority for International Application No. PCT/US2006/000822, dated Jul. 14, 2006, 13 pages.

International Search Report for International Application No. PCT/US2007/015905, dated Apr. 23, 2008, 3 pages.

(56) References Cited

OTHER PUBLICATIONS

International Search Report and Written Opinion of the International Searching Authority for International Application No. PCT/US2007/00610, dated Oct. 11, 2007, 8 pages.

International Search Report and Written Opinion of the International Searching Authority for International Application No. PCT/US2007/005736, dated Aug. 8, 2007, 11 pages.

International Search Report and Written Opinion of the International Searching Authority for International Application No. PCT/US2007/005868, dated Nov. 9, 2007, 7 pages.

International Search Report for International Application No. PCT/US2007/015866, dated Nov. 26, 2007, 3 pages.

International Search Report for International Application No. PCT/US2007/016010, dated Mar. 11, 2008, 4 pages.

International Search Report for International Application No. PCT/US2007/021931, dated Apr. 11, 2008, 3 pages.

International Search Report for International Application No. PCT/US2007/021934, dated Jun. 17, 2008, 3 pages.

International Search Report for International Application No. PCT/US2007/021939, dated Feb. 18, 2008, 2 pages.

International Search Report and Written Opinion of the International Searching Authority for International Application No. PCT/US2008/009604, dated Oct. 27, 2008, 6 pages.

International Search Report and Written Opinion of the International Searching Authority for International Application No. PCT/US2008/009635, dated Oct. 27, 2008, 7 pages.

International Search Report for International Application No. PCT/US2008/065395, dated Sep. 29, 2008, 1 page.

International Search Report for International Application No. PCT/US2008/067025, dated Sep. 8, 2008, 1 page.

Chatterjee et al., "Synthesis of Trisubstituted Alkenes via Olefin Cross-Metathesis," Organic Letters, vol. 1, No. 11, 1999, pp. 1751-1753.

Delaude et al., Metathesis, Kirk-Othmer Encyclopedia of Chemical Technology, Dec. 2005, vol. 26, pp. 920-958.

Ngo et al., Methathesis of Unsaturated Fatty Acids: Synthesis of Long-Chain Unsaturated-[alpha],[omega]-Dicarboxylic Acids, Journal of the American Oil Chemists, Jul. 2006, vol. 83m Iss, 7, p. 629, 9 pgs.

Office Action from counterpart Indian Application No. 1973/MUMNP/2008, dated Mar. 13, 2012, 2 pages.

Šmidovnik, A. et al., "Catalytic Transfer Hydrogenation of Soybean Oil," JAOCS, vol. 69, No. 5, May 1992, pp. 405-409.

Notice of Preliminary Rejection from Korean Application No. 10-2008-7024098, dated Sep. 26, 2013, 10 pages.

* cited by examiner

Internal Olefins

Internal Olefin

60

62

64

66

68

C823

C827

C627

C712

C697

C682

50 where

- L = PCy$_3$, sIMes, Mes, Phobane
- X = H, NO$_2$, SO$_2$N(CH$_3$)$_2$
- X$_2$ = H, N$^+$(C$_2$H$_3$)$_2$CH$_3$
- X$_3$ = H, Phenyl
- R = H, alkyl, aryl, CO$_2$Me

52 where

- L = PCy$_3$, sIMes, Mes, Phobane
- L' = PCy$_3$, Phobane sIMes

Mes

Phobane

COMPOSITIONS COMPRISING METATHESIZED UNSATURATED POLYOL ESTERS

This application claims the benefit under 35 U.S.C. §371 of International Application No. PCT/US2007/005736, filed Mar. 7, 2007, which claims the benefit of U.S. Provisional Patent Application Ser. No. 60/780,125, filed Mar. 7, 2006, which are incorporated herein by reference.

CROSS-REFERENCE TO RELATED APPLICATIONS

This application claims the benefit of U.S. Provisional Application having Ser. No. 60/780,125, filed Mar. 7, 2006, and entitled COMPOSITIONS COMPRISING METATHESIZED UNSATURATED POLYOL ESTERS, the disclosure of which is incorporated herein by reference.

BACKGROUND

Petroleum-based petrolatum and wax compositions are well known and are commonly used in a variety of applications including, for example, creams, lotions, hair preparations, cosmetics, candles, ointments, lubricants, adhesives, and coatings. In view of the non-renewable nature of petroleum, it is highly desirable to provide non-petroleum alternatives for materials, such as petrolatums or waxes that have historically been produced from petroleum.

SUMMARY

In one aspect the invention provides petrolatum-like compositions of matter comprising metathesized unsaturated polyol esters. In many embodiments, the petrolatum-like compositions of the invention are viscous semi-solids at room temperature and, in many embodiments, display properties that are similar to petroleum-derived petrolatum compositions, for example, cone penetration (ASTM D-937), congealing point (ASTM D-938), drop melt point (ASTM D-127), and viscosity (ASTM D-445/D-2161).

In some embodiments, petrolatum-like compositions of the invention comprise a hydrogenated (i.e., including fully and partially hydrogenated) metathesized unsaturated polyol ester that itself displays the desired petrolatum-like properties and that can be used by itself (or with the addition of other minor ingredients) as a petrolatum-like material. Accordingly, in some embodiments, the petrolatum-like compositions consist essentially of or consist of a hydrogenated metathesized unsaturated polyol ester. Typically, the degree of hydrogenation (e.g., as measured by iodine value (IV)) and the extent of oligomerization of the metathesized polyol ester are controlled to provide a hydrogenated metathesized unsaturated polyol ester having petrolatum-like properties.

In some embodiments, the petrolatum-like compositions of the invention comprise a mixture of: (a) a metathesized unsaturated polyol ester; and (b) a polyol ester. In some embodiments, the metathesized unsaturated polyol ester is hydrogenated. The properties of the petrolatum-like composition may be controlled, for example, by varying one or more of the following: (a) the degree of hydrogenation of the metathesized unsaturated polyol ester, (b) the degree of oligomerization of the metathesized unsaturated polyol ester, (c) the degree of hydrogenation of the polyol ester, and/or (d) the relative amounts of components (i) and (ii) in the composition.

In some embodiments, the metathesized unsaturated polyol ester is a metathesized vegetable oil, for example, metathesized soybean oil, metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized sunflower oil, metathesized linseed oil, metathesized palm kernel oil, metathesized tung oil, and metathesized castor oil. In other embodiments, the metathesized unsaturated polyol ester is a metathesized animal fat, for example, metathesized lard, metathesized tallow, metathesized chicken fat (i.e., yellow grease), and metathesized fish oil. Mixtures of the foregoing may also be useful.

In exemplary embodiments, the metathesized unsaturated polyol ester is hydrogenated (i.e., including fully and partially hydrogenated). Representative examples include hydrogenated metathesized vegetable oil, for example, hydrogenated metathesized soybean oil, hydrogenated metathesized canola oil, hydrogenated metathesized rapeseed oil, hydrogenated metathesized coconut oil, hydrogenated metathesized corn oil, hydrogenated metathesized cottonseed oil, hydrogenated metathesized olive oil, hydrogenated metathesized palm oil, hydrogenated metathesized peanut oil, hydrogenated metathesized safflower oil, hydrogenated metathesized sesame oil, hydrogenated metathesized sunflower oil, hydrogenated metathesized linseed oil, hydrogenated metathesized palm kernel oil, hydrogenated metathesized tung oil, hydrogenated metathesized castor oil, hydrogenated metathesized lard, hydrogenated metathesized tallow, hydrogenated metathesized chicken fat (yellow grease), and hydrogenated metathesized fish oil. Mixtures of the foregoing may also be useful.

In many embodiments, the metathesized unsaturated polyol ester or hydrogenated metathesized unsaturated polyol ester comprises one or more of metathesis monomers, metathesis dimers, metathesis trimers, metathesis tetramers, metathesis pentamers, and higher order metathesis oligomers. Typically, the metathesized unsaturated polyol ester or hydrogenated metathesized unsaturated polyol ester comprises a mixture of metathesis monomers, metathesis dimers, metathesis trimers, metathesis tetramers, metathesis pentamers, and higher order metathesis oligomers.

In many embodiments, the polyol ester component of the petrolatum-like composition comprises a natural oil, such as a vegetable oil, algae oil, or an animal fat. Examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, and the like. Mixtures may also be useful. The vegetable oil may be partially hydrogenated, winterized, or partially hydrogenated and winterized. In an exemplary embodiment, the vegetable oil is refined, bleached, and deodorized (RBD) soybean oil.

In many embodiments, the metathesized unsaturated polyol ester or hydrogenated metathesized unsaturated polyol ester is present in the petrolatum-like composition in an amount of about 50% wt. or less, for example, about 40% wt. or less, about 30% weight or less, about 25% wt. or less, about 20% wt. or less, about 15% wt. or less, or about 10% wt. or less. In an exemplary embodiment, the petrolatum-like composition comprises about 30% wt. or less hydrogenated metathesized soybean oil, and about 70% wt. or greater refined, bleached, and deodorized (i.e., RBD) soybean oil. In another exemplary embodiment, the petrolatum-like composition comprises about 5% wt. to about 25% wt. hydrogenated metathesized soybean oil, and about 75% wt. to about 95% wt. soybean oil.

In some embodiments, the petrolatum-like compositions of the invention have a cone penetration @ 77° F. (25° C.) (ASTM D-937) that is similar to petroleum-derived petrolatum. For example, in some embodiments, the compositions have a cone penetration @ 77° F. (25° C.) of about 100 dmm to about 300 dmm. In exemplary embodiments, the compositions have a cone penetration @ 77° F. (25° C.) of about 150 dmm to about 160 dmm.

In some embodiments, the petrolatum-like compositions of the invention have a congealing point (ASTM D938) that is similar to petroleum-derived petrolatum. For example, in some embodiments the compositions have a congealing point of about 100° F. to about 140° F. (37.8° C. to 60° C.). In exemplary embodiments, the compositions have a congealing point of about 105° F. to about 135° F. (40.6° C. to 57.2° C.).

In some embodiments, the petrolatum-like compositions of the invention have a drop melt point (ASTM D-127) that is similar to petroleum-derived petrolatum. For example, in some embodiments the compositions have a drop melt point of about 100° F. to about 150° F. (37.8° C. to 65.6° C.).

In some embodiments, the petrolatum-like compositions of the invention have a viscosity at 210° F. (ASTM D-445 and D-2161) that is similar to that of petroleum-derived petrolatum. For example, in some embodiments the compositions have a kinematic viscosity of 100 SUS or less, more typically about 40 SUS to about 90 SUS, or about 55 to about 80 SUS.

Petrolatum-like compositions of the invention may be used, for example, as substitutes for petroleum-derived petrolatum compositions. Representative examples of typical applications include personal care items (e.g., cosmetics, lip balm, lipstick, hand cleaners, hair dressings, ointments, sun care products, moisturizers, pharmaceutical ointments, fragrance sticks, and perfume carriers); plastics (e.g., a processing aid for PVC); food (e.g., cheese coatings, baking grease); telecommunications (e.g., cable filling or flooding compounds); industrial applications (e.g., grain dust suppressant, rust preventative coatings, adhesives, toilet boil rings, bone guard, and textile coatings).

In another aspect, the invention provides emulsions comprising metathesized unsaturated polyol esters. The metathesized unsaturated polyol ester may be hydrogenated, for example, fully or partially hydrogenated. The emulsions may be oil-in-water emulsions or water-in-oil emulsions. The oil phase of the emulsion may have petrolatum-like properties or may be a metathesized wax. In some embodiments, the oil-in-water emulsions comprise: (a) a dispersed phase comprising a metathesized unsaturated polyol ester, and (b) a continuous phase comprising water. In other embodiments, the oil-in-water emulsions comprise: (a) a dispersed phase comprising a mixture of (i) a metathesized unsaturated polyol ester, and (ii) a polyol ester; and (b) a continuous phase comprising water.

Emulsions of the invention may be used, for example, as replacements for petroleum-derived wax emulsions. Representative examples of applications for the emulsions of the invention include in building materials (e.g., coatings for oriented strand board (OSB) or medium density fiberboard, lumber coatings); metal coatings (e.g., slip coating for cans, coil coatings); corrugated paperboard coatings; inks (e.g., additive to improve rub or scuff resistance in water based inks); fiberglass (e.g., antiblock or lubricant); molded latex articles (e.g., mold release for gloves or condoms); textiles (e.g., sizing agent or thread lubricant); floor finish (e.g., additive to impart rub resistance); flexible films (e.g., processing aid); coatings (e.g., to add water repellency to deck stains or wood varnishes); and fruit/vegetable coating (e.g., as a moisture barrier coating); cosmetic and personal care formulations (e.g., face, hand and body lotions/creams, lip care products, hair care products as a moisturizer or moisture barrier coating).

BRIEF DESCRIPTION OF THE DRAWINGS

The invention will be described further in connection with the attached drawings, wherein like reference numbers have been used to indicate like parts and wherein.

DETAILED DESCRIPTION

Metathesized Unsaturated Polyol Ester

Figure 1:
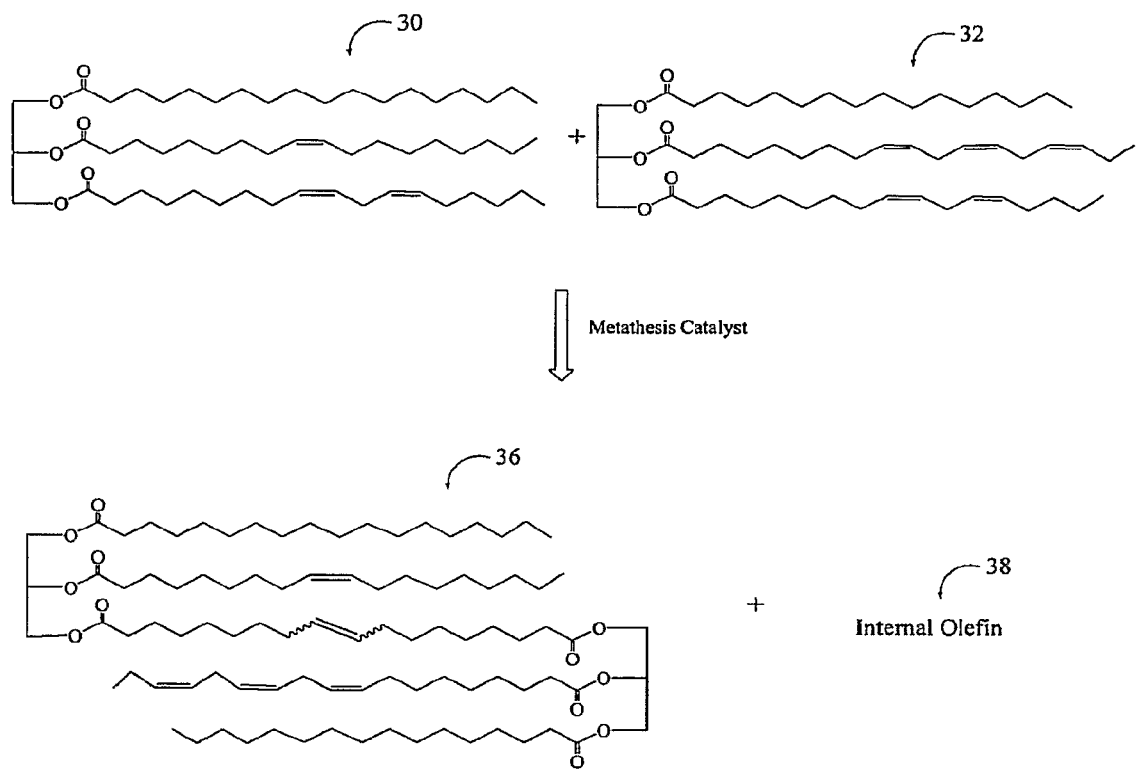
FIG. 1 is an exemplary metathesis reaction scheme.

The petrolatum-like compositions and the emulsions of the invention comprise a metathesized unsaturated polyol ester. In some embodiments the metathesized unsaturated polyol esters is hydrogenated, for example, partially or fully hydrogenated.

A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis). Self-metathesis may be represented schematically as shown in Equation I.

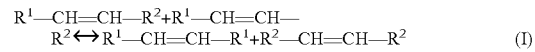

(I)

where $R^1$ and $R^2$ are organic groups.

Cross-metathesis may be represented schematically as shown in Equation II.

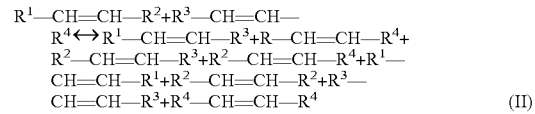

(II)

where $R^1$, $R^2$, $R^3$, and $R^4$ are organic groups.

When the unsaturated polyol ester comprises molecules that have more than one carbon-carbon double bond (i.e., a polyunsaturated polyol ester), self-metathesis results in oligomerization of the unsaturated polyol ester. The self-metathesis reaction results in the formation of metathesis dimers, metathesis trimers, and metathesis tetramers. Higher order metathesis oligomers, such as metathesis pentamers and metathesis hexamers, may also be formed by continued self-metathesis.

As a starting material, metathesized unsaturated polyol esters are prepared from one or more unsaturated polyol esters. As used herein, the term "unsaturated polyol ester" refers to a compound having two or more hydroxyl groups wherein at least one of the hydroxyl groups is in the form of an ester and wherein the ester has an organic group including at least one carbon-carbon double bond. In many embodiments, the unsaturated polyol ester can be represented by the general structure (I):

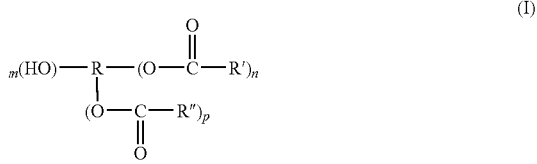

where n≥1;
m≥0;
p≥0;
(n+m+p)≥2;
R is an organic group;
R' is an organic group having at least one carbon-carbon double bond; and
R" is a saturated organic group.

In many embodiments of the invention, the unsaturated polyol ester is an unsaturated polyol ester of glycerol. Unsaturated polyol esters of glycerol have the general structure (II):

where —X, —Y, and —Z are independently selected from the group consisting of:

—OH; —(O—C(=O)—R'); and —(O—C(=O)—R");

where —R' is an organic group having at least one carbon-carbon double
bond and —R" is a saturated organic group.

In structure (II), at least one of —X, —Y, or —Z is —(O—C(=O)—R').

In some embodiments, R' is a straight or branched chain hydrocarbon having about 50 or less carbon atoms (e.g., about 36 or less carbon atoms or about 26 or less carbon atoms) and at least one carbon-carbon double bond in its chain. In some embodiments, R' is a straight or branched chain hydrocarbon having about 6 carbon atoms or greater (e.g., about 10 carbon atoms or greater or about 12 carbon atoms or greater) and at least one carbon-carbon double bond in its chain. In some embodiments, R' may have two or more carbon-carbon double bonds in its chain. In other embodiments, R' may have three or more double bonds in its chain. In exemplary embodiments, R' has 17 carbon atoms and 1 to 3 carbon-carbon double bonds in its chain. Representative examples of R' include:

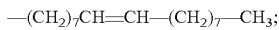

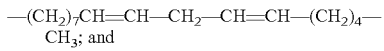

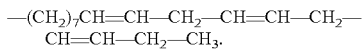

In some embodiments, R" is a saturated straight or branched chain hydrocarbon having about 50 or less carbon atoms (e.g., about 36 or less carbon atoms or about 26 or less carbon atoms). In some embodiments, R" is a saturated straight or branched chain hydrocarbon having about 6 carbon atoms or greater (e.g., about 10 carbon atoms or greater or about 12 carbon atoms or greater. In exemplary embodiments, R" has 15 carbon atoms or 17 carbon atoms.

Sources of unsaturated polyol esters of glycerol include synthesized oils, natural oils (e.g., vegetable oils, algae oils, and animal fats), combinations of these, and the like. Representative examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, combinations of these, and the like. Representative examples of animal fats include lard, tallow, chicken fat, yellow grease, fish oil, combinations of these, and the like. A representative example of a synthesized oil includes tall oil, which is a byproduct of wood pulp manufacture.

In an exemplary embodiment, the vegetable oil is soybean oil, for example, refined, bleached, and deodorized soybean oil (i.e., RBD soybean oil). Soybean oil is an unsaturated polyol ester of glycerol that typically comprises about 95% weight or greater (e.g., 99% weight or greater) triglycerides of fatty acids. Major fatty acids in the polyol esters of soybean oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Soybean oil is a highly unsaturated vegetable oil with many of the triglyceride molecules having at least two unsaturated fatty acids (i.e., a polyunsaturated triglyceride).

In exemplary embodiments, an unsaturated polyol ester is self-metathesized in the presence of a metathesis catalyst to form a metathesized composition. In many embodiments, the metathesized composition comprises one or more of: metathesis monomers, metathesis dimers, metathesis trimers, metathesis tetramers, metathesis pentamers, and higher order metathesis oligomers (e.g., metathesis hexamers). A metathesis dimer refers to a compound formed when two unsaturated polyol ester molecules are covalently bonded to one another by a self-metathesis reaction. In many embodiments, the molecular weight of the metathesis dimer is greater than the molecular weight of the individual unsaturated polyol ester molecules from which the dimer is formed. A metathesis trimer refers to a compound formed when three unsaturated polyol ester molecules are covalently bonded together by metathesis reactions. In many embodiments, a metathesis trimer is formed by the cross-metathesis of a metathesis dimer with an unsaturated polyol ester. A metathesis tetramer refers to a compound formed when four unsaturated polyol ester molecules are covalently bonded together by metathesis reactions. In many embodiments, a metathesis tetramer is formed by the cross-metathesis of a metathesis trimer with an unsaturated polyol ester. Metathesis tetramers may also be formed, for example, by the cross-metathesis of two metathesis dimers. Higher order metathesis products may also be formed. For example, metathesis pentamers and metathesis hexamers may also be formed.

Figure 1A:
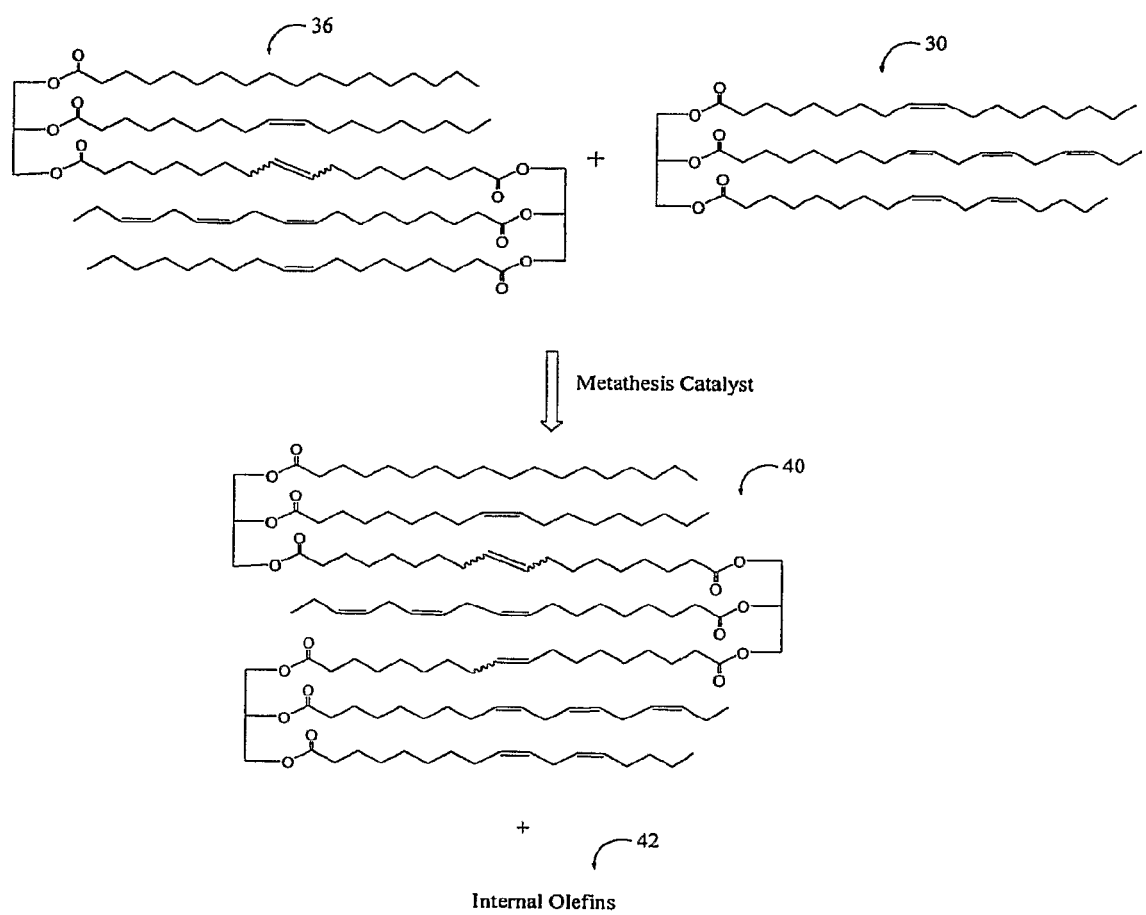
FIG. 1A is an exemplary metathesis reaction scheme.
Figure 1B:
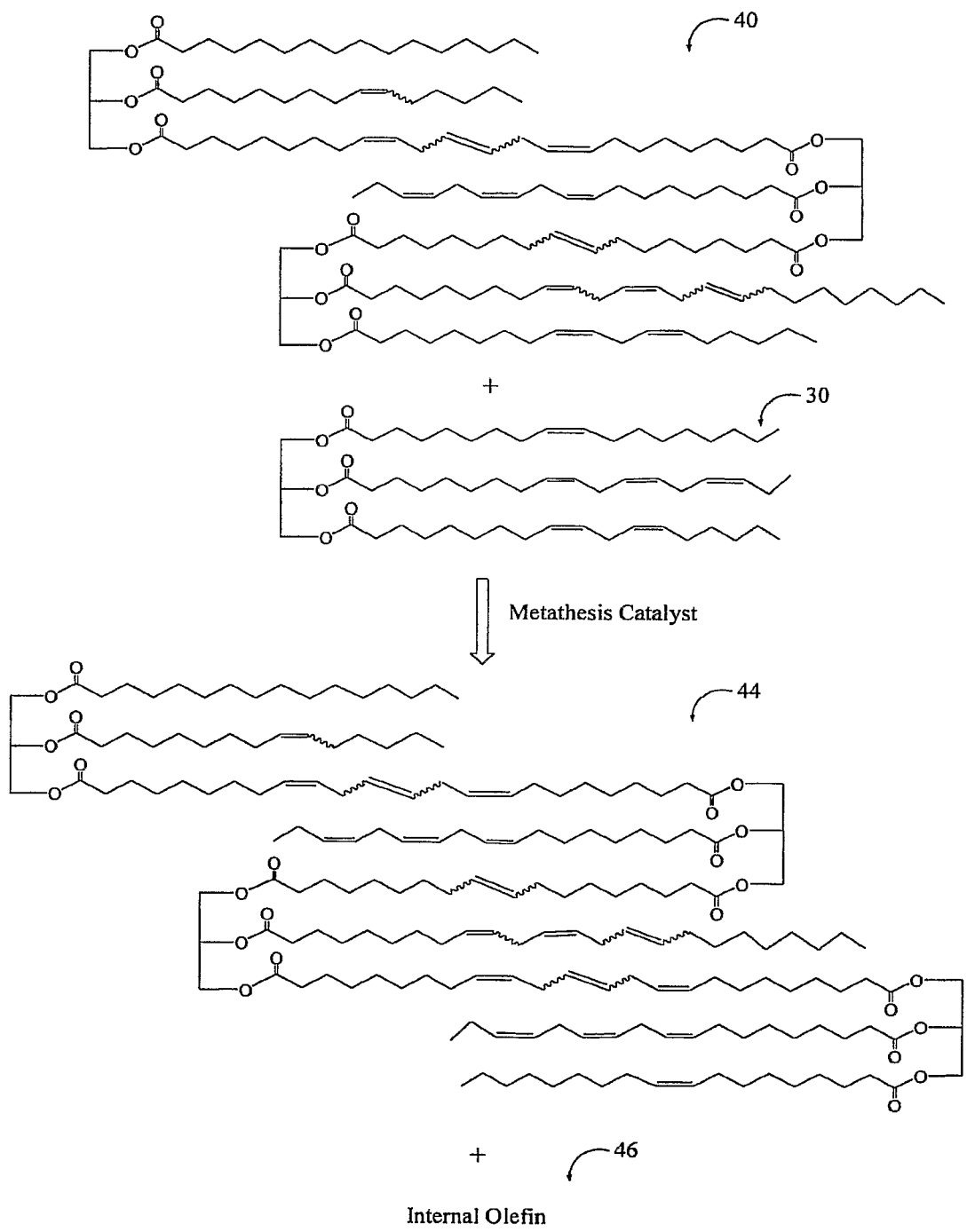
FIG. 1B is an exemplary metathesis reaction scheme.
Figure 1C:
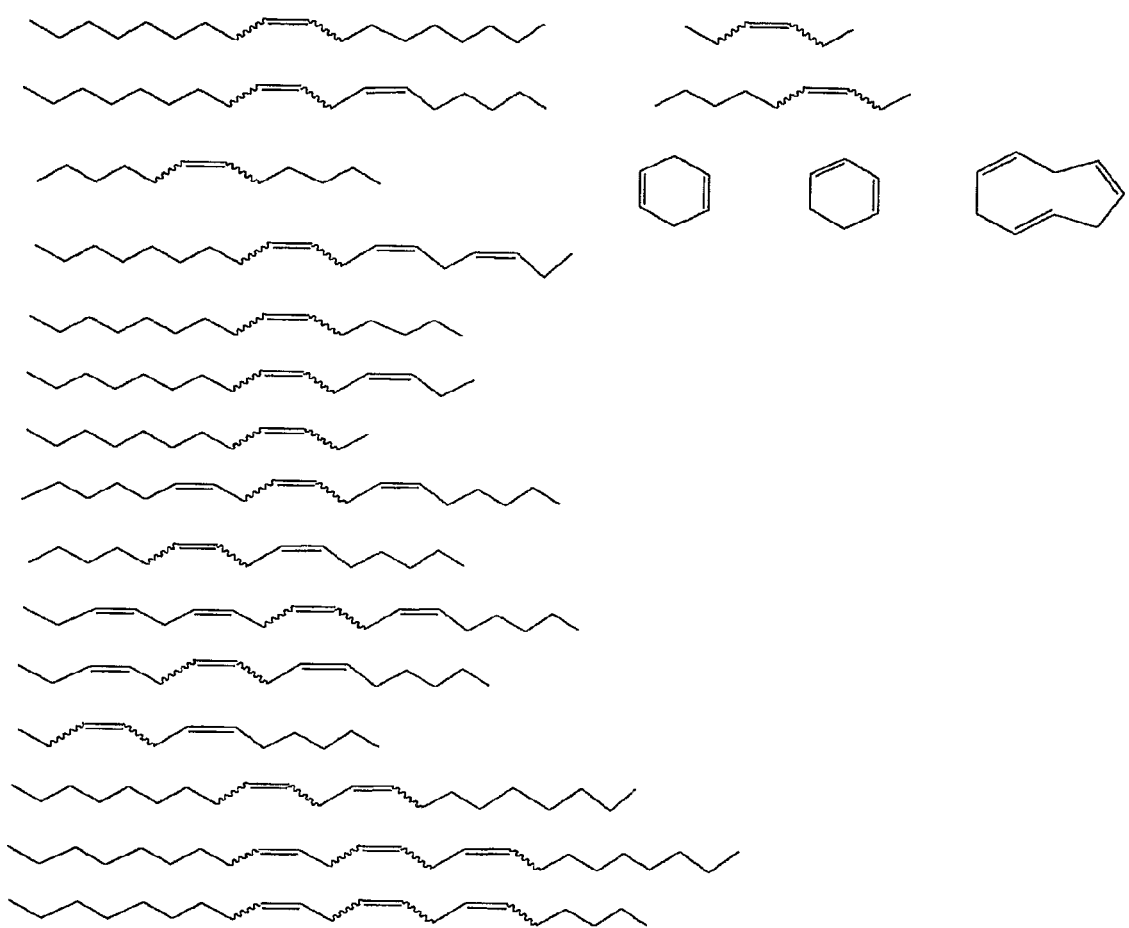
FIG. 1C displays certain internal and cyclic olefins that may be by products of the metathesis reactions of FIGS. 1-1B.

An exemplary metathesis reaction scheme is shown in FIGS. 1-1B. As shown in FIG. 1, triglyceride 30 and triglyceride 32 are self metathesized in the presence of a metathesis catalyst 34 to form metathesis dimer 36 and internal olefin 38. As shown in FIG. 1A, metathesis dimer 36 may further react with another triglyceride molecule 30 to form metathesis trimer 40 and internal olefin 42. As shown in FIG. 1B, metathesis trimer 40 may further react with another triglyceride molecule 30 to form metathesis tetramer 44 and internal olefin 46. In this way, the self-metathesis results in the formation of a distribution of metathesis monomers, metathesis dimers, metathesis trimers, metathesis tetramers, and higher order metathesis oligomers. Also typically present are metathesis monomers, which may comprise unreacted triglyceride, or triglyceride that has reacted in the metathesis reaction but has not formed an oligomer. The self-metathesis reaction also results in the formation of internal olefin compounds that may be linear or cyclic. FIG. 1C shows representative examples of certain linear and cyclic internal olefins 38, 42, 46 that may be formed during a self-metathesis reaction. If the metathesized polyol ester is hydrogenated, the linear and cyclic olefins would typically be converted to the corresponding saturated linear and cyclic hydrocarbons. The linear/cyclic olefins and saturated linear/cyclic hydrocarbons may remain in the metathesized polyol ester or they may be removed or partially removed from the metathesized polyol ester using known stripping techniques. It should be understood that FIG. 1 provides merely exemplary embodiments of metathesis reaction schemes and compositions that may result therefrom.

The relative amounts of monomers, dimers, trimers, tetramers, pentamers, and higher order oligomers may be determined by chemical analysis of the metathesized polyol ester including, for example, by liquid chromatography, specifically gel permeation chromatography (GPC). For example, the relative amount of monomers, dimers, trimers, tetramers and higher unit oligomers may be characterized, for example, in terms of "area %" or wt. %. That is, an area percentage of a GPC chromatograph can be correlated to weight percentage. In some embodiments, the metathesized unsaturated polyol ester comprises at least about 30 area % or wt. % tetramers and/or other higher unit oligomers or at least about 40 area % or wt. % tetramers and/or other higher unit oligomers. In some embodiments, the metathesized unsaturated polyol ester comprises no more than about 60 area % or wt. % tetramers and/or other higher unit oligomers or no more than about 50 area % or wt. % tetramers and/or other higher unit oligomers. In other embodiments, the metathesized unsaturated polyol ester comprises no more than about 1 area % or wt. % tetramers and/or other higher unit oligomers. In some embodiments, the metathesized unsaturated polyol ester comprises at least about 5 area % or wt. % dimers or at least about 15 area % or wt. % dimers. In some embodiments, the metathesized unsaturated polyol ester comprises no more than about 25 area % or wt. % dimers. In some of these embodiments, the metathesized unsaturated polyol ester comprises no more than about 20 area % or wt. % dimers or no more than about 10 area % or wt. % dimers. In some embodiments, the metathesized unsaturated polyol ester comprises at least 1 area % or wt. % trimers. In some of these embodiments, the metathesized unsaturated polyol ester comprises at least about 10 area % or wt. % trimers. In some embodiments, the metathesized unsaturated polyol ester comprises no more than about 20 area % or wt. % trimers or no more than about 10 area % or wt. % trimers. According to some of these embodiments, the metathesized unsaturated polyol ester comprises no more than 1 area % or wt. % trimers.

In some embodiments, the unsaturated polyol ester is partially hydrogenated before being metathesized. For example, in some embodiments, the soybean oil is partially hydrogenated to achieve an iodine value (IV) of about 120 or less before subjecting the partially hydrogenated soybean oil to metathesis.

In some embodiments, the hydrogenated metathesized polyol ester has an iodine value (IV) of about 100 or less, for example, about 90 or less, about 80 or less, about 70 or less, about 60 or less, about 50 or less, about 40 or less, about 30 or less, about 20 or less, about 10 or less or about 5 or less.

Figure 2:
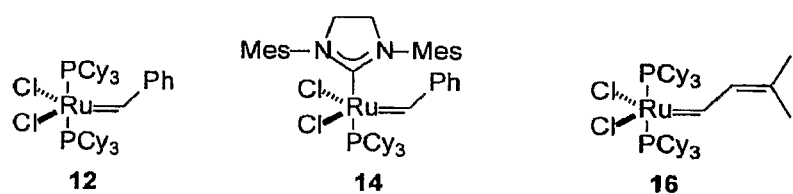
FIG. 2 is a figure showing exemplary ruthenium-based metathesis catalysts.
Figure 3:
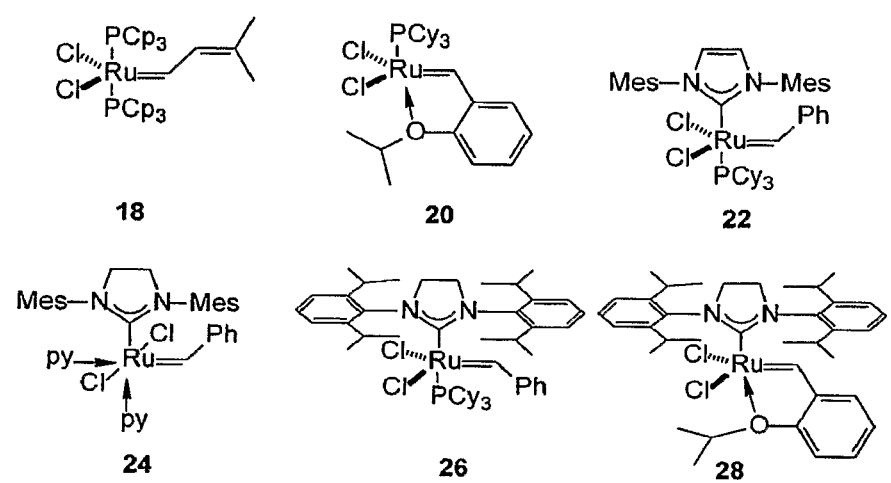
FIG. 3 is a figure showing exemplary ruthenium-based metathesis catalysts.
Figure 4:
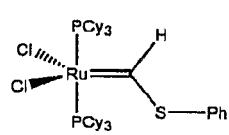
FIG. 4 is a figure showing exemplary ruthenium-based metathesis catalysts.
Figure 4:
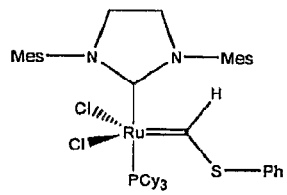
Figure 4:
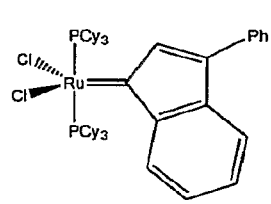
Figure 4:
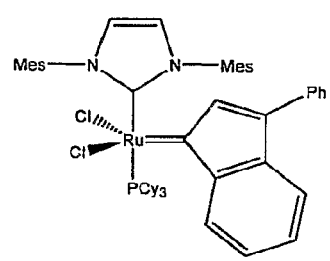
Figure 4:
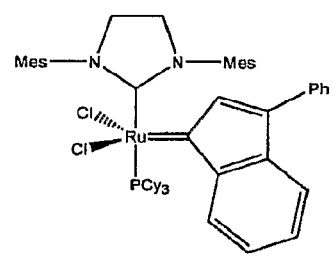
Figure 5:
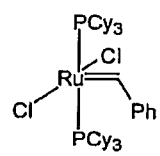
FIG. 5 is a figure showing exemplary ruthenium-based metathesis catalysts.
Figure 5:
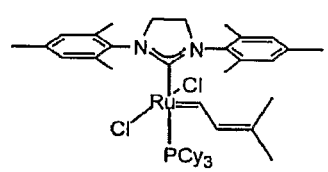
Figure 5:
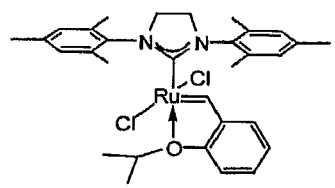
Figure 5:
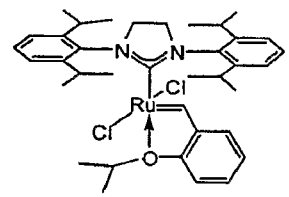
Figure 5:
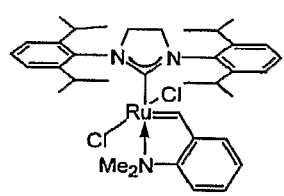
Figure 5:
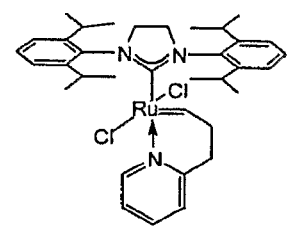
Figure 6:
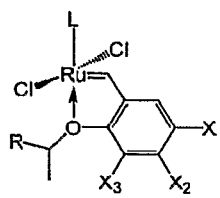
FIG. 6 is a figure showing exemplary ruthenium-based metathesis catalysts.
Figure 6:
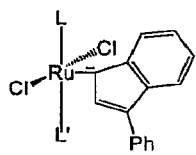
Figure 6:
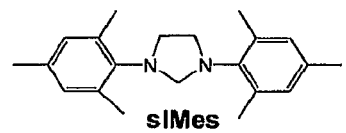
Figure 6:
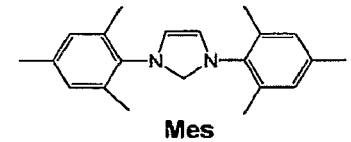

Method of Making Metathesized Unsaturated Polyol Ester:

The self-metathesis of unsaturated polyol esters is typically conducted in the presence of a catalytically effective amount of a metathesis catalyst. The term "metathesis catalyst" includes any catalyst or catalyst system that catalyzes a metathesis reaction. Any known or future-developed metathesis catalyst may be used, alone or in combination with one or more additional catalysts. Exemplary metathesis catalysts include metal carbene catalysts based upon transition metals, for example, ruthenium, molybdenum, osmium, chromium, rhenium, and tungsten. Referring to FIG. 2, exemplary ruthenium-based metathesis catalysts include those represented by structures 12 (commonly known as Grubbs's catalyst), 14 and 16. Referring to FIG. 3, structures 18, 20, 22, 24, 26, and 28 represent additional ruthenium-based metathesis catalysts. Referring to FIG. 4, structures 60, 62, 64, 66, and 68 represent additional ruthenium-based metathesis catalysts. Referring to FIG. 5, catalysts C627, C682, C697, C712, and C827 represent still additional ruthenium-based catalysts. Referring to FIG. 6, general structures 50 and 52 represent additional ruthenium-based metathesis catalysts of the type reported in *Chemical & Engineering News*; Feb. 12, 2007, at pages 37-47. In the structures of FIGS. 2-6, Ph is phenyl, Mes is mesityl, py is pyridine, Cp is cyclopentyl, and Cy is cyclohexyl. Techniques for using the metathesis catalysts are known in the art (see, for example, U.S. Pat. Nos. 7,102,047; 6,794,534; 6,696,597; 6,414,097; 6,306,988; 5,922,863; 5,750,815; and metathesis catalysts with ligands in U.S. Publication No. 2007/0004917 A1). Metathesis catalysts as shown, for example, in FIGS. 2-5 are manufactured by Materia, Inc. (Pasadena, Calif.).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne- or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

The metathesis process can be conducted under any conditions adequate to produce the desired metathesis products. For example, stoichiometry, atmosphere, solvent, temperature and pressure can be selected to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1. In some embodiments, an amount of about 1 to about 10 ppm, or about 2 ppm to about 5 ppm, of the metathesis catalyst per double bond of the starting composition (i.e., on a mole/mole basis) is used.

The metathesis reaction temperature may be a rate-controlling variable where the temperature is selected to provide a desired product at an acceptable rate. The metathesis temperature may be greater than −40° C., may be greater than about −20° C., and is typically greater than about 0° C. or greater than about 20° C. Typically, the metathesis reaction temperature is less than about 150° C., typically less than about 120° C. An exemplary temperature range for the metathesis reaction ranges from about 20° C. to about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 10 kPa, in some embodiments greater than about 30 kP, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa.

In some embodiments, the metathesis reaction is catalyzed by a system containing both a transition and a non-transition metal component. The most active and largest number of catalyst systems are derived from Group VI A transition metals, for example, tungsten and molybdenum.

Hydrogenation:

In some embodiments, the unsaturated polyol ester is partially hydrogenated before it is subjected to the metathesis reaction. Partial hydrogenation of the unsaturated polyol ester reduces the number of double bonds that are available for in the subsequent metathesis reaction. In some embodiments, the unsaturated polyol ester is metathesized to form a metathesized unsaturated polyol ester, and the metathesized unsaturated polyol ester is then hydrogenated (e.g., partially or fully hydrogenated) to form a hydrogenated metathesized unsaturated polyol ester.

Hydrogenation may be conducted according to any known method for hydrogenating double bond-containing compounds such as vegetable oils. In some embodiments, the unsaturated polyol ester or metathesized unsaturated polyol ester is hydrogenated in the presence of a nickel catalyst that has been chemically reduced with hydrogen to an active state. Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

In some embodiments, the hydrogenation catalyst comprising, for example, nickel, copper, palladium, platinum, molybdenum, iron, ruthenium, osmium, rhodium, or iridium. Combinations of metals may also be used. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. In some embodiments, the support comprises porous silica (e.g., kieselguhr, infusorial, diatomaceous, or siliceous earth) or alumina. The catalysts are characterized by a high nickel surface area per gram of nickel.

In some embodiments, the particles of supported nickel catalyst are dispersed in a protective medium comprising hardened triacylglyceride, edible oil, or tallow. In an exemplary embodiment, the supported nickel catalyst is dispersed in the protective medium at a level of about 22 wt. % nickel.

In some embodiments, the supported nickel catalysts are of the type reported in U.S. Pat. No. 3,351,566 (Taylor et al.). These catalysts comprise solid nickel-silica having a stabilized high nickel surface area of 45 to 60 sq. meters per gram and a total surface area of 225 to 300 sq. meters per gram. The catalysts are prepared by precipitating the nickel and silicate ions from solution such as nickel hydrosilicate onto porous silica particles in such proportions that the activated catalyst contains 25 wt. % to 50 wt. % nickel and a total silica content of 30 wt. % to 90 wt %. The particles are activated by calcining in air at 600° F. to 900° F., then reducing with hydrogen.

Useful catalysts having a high nickel content are described in EP 0 168 091, wherein the catalyst is made by precipitation of a nickel compound. A soluble aluminum compound is added to the slurry of the precipitated nickel compound while the precipitate is maturing. After reduction of the resultant catalyst precursor, the reduced catalyst typically has a nickel surface area of the order of 90 to 150 sq. m per gram of total nickel. The catalysts have a nickel/aluminum atomic ratio in the range of 2 to 10 and have a total nickel content of more than about 66% by weight.

Useful high activity nickel/alumina/silica catalysts are described in EP 0 167 201. The reduced catalysts have a high nickel surface area per gram of total nickel in the catalyst.

Useful nickel/silica hydrogenation catalysts are described in U.S. Pat. No. 6,846,772. The catalysts are produced by heating a slurry of particulate silica (e.g. kieselguhr) in an aqueous nickel amine carbonate solution for a total period of at least 200 minutes at a pH above 7.5, followed by filtration, washing, drying, and optionally calcination. The nickel/silica hydrogenation catalysts are reported to have improved filtration properties. U.S. Pat. No. 4,490,480 reports high surface area nickel/alumina hydrogenation catalysts having a total nickel content of 5% to 40% wt.

Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated (e.g., RBD soybean oil or metathesized RBD soybean oil). The material is then heated to a desired temperature. Typically, the temperature ranges from about 50° C. to 350° C., for example, about 100° C. to 300° C. or about 150° C. to 250° C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (e.g., RBD soybean oil or metathesized RBD soybean oil). When the material to be hydrogenated reaches the desired temperature, the slurry of hydrogenation catalyst is added to the reaction vessel. Hydrogen gas is then pumped into the reaction vessel to achieve a desired pressure of $H_2$ gas. Typically, the $H_2$ gas pressure ranges from about 15 to 3000 psig, for example, about 15 psig to 90 psig. As the gas pressure increases, more specialized high-pressure processing equipment may be required. Under these conditions the hydrogenation reaction begins and the temperature is allowed to increase to the desired hydrogenation temperature (e.g., about 120° C. to 200° C.) where it is maintained by cooling the reaction mass, for example, with cooling coils. When the desired degree of hydrogenation is reached, the reaction mass is cooled to the desired filtration temperature.

The amount of hydrogenation catalysts is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of about 10 wt. % or less, for example, about 5 wt. % or less or about 1 wt. % or less.

After hydrogenation, the hydrogenation catalyst may be removed from the hydrogenated product using known techniques, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the metathesized product directly or it may be applied to the filter. Representative examples of filtering aids include diatomaceous earth, silica, alumina, and carbon. Typically, the filtering aid is used in an amount of about 10 wt. % or less, for example, about 5 wt. % or less or about 1 wt. % or less. Other filtering techniques and filtering aids may also be employed to remove the used hydrogenation catalyst. In other embodiments the hydrogenation catalyst is removed using centrifugation followed by decantation of the product.

Petrolatum-Like Compositions:

Petrolatum-like compositions of the invention comprise a metathesized unsaturated polyol ester. In some embodiments, the metathesized unsaturated polyol ester is hydrogenated. Hydrogenation may be partial hydrogenation or full hydrogenation. The degree of hydrogenation may be controlled in order to achieve the desired properties. For example, as the degree of hydrogenation increases, the melting point of the composition increases providing a composition that is more solid-like (i.e., harder) at room temperature.

In some embodiments, the hydrogenated metathesized unsaturated polyol ester itself has petrolatum-like properties. In some embodiments, the petrolatum-like composition comprises a mixture of: (a) a metathesized unsaturated polyol ester; and (b) a polyol ester. In many embodiments, the metathesized unsaturated polyol ester is hydrogenated (e.g., partially hydrogenated or fully hydrogenated). Typically, in these embodiments, the hydrogenated metathesized unsaturated polyol ester is a solid or a high viscosity semi-solid (e.g., a wax) at room temperature, and the polyol ester is a liquid at room temperature. When mixed together, the two materials form a composition that has petrolatum-like properties.

The hydrogenated metathesized unsaturated polyol ester and the polyol ester may be mixed in desired amounts to form a petrolatum-like composition of the invention having the desired petrolatum-like properties. Typically, as the amount of hydrogenated metathesized polyol ester in the composition increases, the viscosity of the resulting petrolatum-like composition increases. In some embodiments, the hydrogenated metathesized polyol ester is present in an amount up to about 75% wt., for example, up to about 50% wt., up to about 40% wt., up to about 35% wt., up to about 30% wt., or up to about 25% wt. In exemplary embodiments, the hydrogenated metathesized polyol ester is present in an amount from about 5% wt. to about 50% wt. or from about 5% wt. to 25% wt.

Representative examples of polyol esters for use in the petrolatum-like compositions include natural oils, for example, vegetable oils, algae oils, animal fats, or mixtures thereof. Representative examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, and the like, and mixtures thereof. Examples of animal fats include lard, tallow, chicken fat (yellow grease), fish oil, and mixtures thereof. Preferred natural oils are liquids at room temperature and are stable over time. In an exemplary embodiment, the natural oil is refined, bleached, and deodorized soybean oil (i.e., RBD soybean oil). Suitable RBD soybean oil can be obtained commercially from Cargill, Incorporated. (Minneapolis, Minn.).

In some embodiments, the natural oil may be hydrogenated (e.g., fully or partially hydrogenated) in order to improve the stability of the oil or to modify its viscosity or other properties. Representative techniques for hydrogenating natural oils are known in the art and are discussed herein. For example, hydrogenation of certain vegetable oils is reported in Chapter 11 of Bailey, A. E.; *Baileys Industrial Oil and Fat Products; Volume 2: Edible Oil & Fat Products: Oils and Oil Seeds; 5th* Edition (1996) edited by Y. H. Hui (ISBN 0-471-59426-1). In some embodiments, the natural oil is RBD soybean oil that has been lightly hydrogenated to achieve an Iodine Value (IV) of about 100 or greater, for example, about 100 to about 110. Suitable lightly hydrogenated RBD soybean oil is commercially available from Cargill, Incorporated (Minneapolis, Minn.).

In some embodiments, the natural oil is winterized. Winterization refers to the process of: (1) removing waxes and other non-triglyceride constituents, (2) removing naturally occurring high-melting triglycerides, and (3) removing high-melting triglycerides formed during partial hydrogenation. Winterization may be accomplished by known methods including, for example, cooling the oil at a controlled rate in order to cause crystallization of the higher melting components that are to be removed from the oil. The crystallized high melting components are then removed from the oil by filtration resulting in winterized oil. Winterized soybean oil is commercially available from Cargill, Incorporated (Minneapolis, Minn.).

In some embodiments, the polyol ester may comprise a mixture of two or more natural oils. For example, in some embodiments, the polyol ester may comprise a mixture of fully-hydrogenated soybean oil and partially or non-hydrogenated soybean oil. In other embodiments, the polyol ester may comprise a mixture of partially hydrogenated soybean oil and non-hydrogenated soybean oil. In yet other embodiments, the polyol ester may comprise a mixture of two or more different natural oils, for example, a mixture of soybean oil and castor oil. In exemplary embodiments, the petrolatum-like composition comprises a mixture of: (i) a hydrogenated metathesized vegetable oil; and (ii) a vegetable oil. For example, in some embodiments, the petrolatum-like composition comprises a mixture of: (i) hydrogenated metathesized soybean oil (HMSBO); and (ii) soybean oil. In some embodiments, the soybean oil is partially hydrogenated, for example, having an iodine value (IV) of about 80 to 120.

In some embodiments, the petrolatum-like compositions of the invention have an iodine value (IV) that ranges from about 5 to about 100, more typically ranging from about 20 to about 100. In some embodiments, the iodine value ranges from about 70 to about 90.

In some embodiments, the petrolatum-like compositions have a cone penetration @ 77° F. (25° C.) (ASTM D-937) that is similar to petroleum-derived petrolatum. For example, in some embodiments, the compositions may have a cone penetration @ 77° F. (25° C.) of about 100 dmm to about 300 dmm. In exemplary embodiments, the compositions have a cone penetration @ 77° F. (25° C.) of about 150 dmm to about 160 dmm.

In some embodiments, the petrolatum-like compositions have a congealing point (ASTM D-938) that is similar to petroleum-derived petrolatum. For example, in some embodiments the compositions may have a congealing point of about 100° F. to about 140° F. (37.8° C. to 60° C.). In exemplary embodiments, the compositions have a congealing point of about 105° F. to about 135° F. (40.6° C. to 57.2° C.).

In some embodiments, the petrolatum-like compositions have a drop melt point (ASTM D-127) that is similar to petroleum-derived petrolatum. For example, in some embodiments the compositions may have a drop melt point of about 100° F. to about 150° F. (37.80° C. to 65.6° C.).

In some embodiments, the petrolatum-like compositions have a viscosity at 210° F. (ASTM D445 and D-2161) that is similar to that of petroleum-derived petrolatum. For example, in some embodiments the compositions have a kinematic viscosity of about 100 SUS or less, more typically about 40 SUS to about 90 SUS, or about 55 to about 80 SUS.

Method of Manufacturing Petrolatum-Like Compositions:

A petrolatum-like composition comprising a mixture of (i) a hydrogenated metathesized unsaturated polyol ester, and (ii) a polyol ester may be prepared, for example, by the following general process. First, the polyol ester (e.g., soybean oil) is heated to a temperature of about 100° F. to 150° F. (37.8° C. to 65.6° C.). Next, the hydrogenated metathesized unsaturated polyol ester (e.g., hydrogenated metathesized soybean oil) is added to the polyol ester and the two materials are mixed together to form a uniform composition. Optional ingredients such as stabilizers may be added in some embodiments. After thoroughly mixing, the resulting mixture is allowed to cool upon which it forms petrolatum-like composition.

Stabilizers:

In some embodiments, the petrolatum-like compositions further includes one or more stabilizers. Representative stabilizers include antioxidants (e.g., tocopherols or BHT) or emulsifiers. Typically, stabilizers are added in an amount less than about 2% wt. although other amounts may also be useful.

Representative Applications of Petrolatum-Like Compositions:

Petrolatum-like compositions of the invention may be suitable in a wide variety of applications including, for example, applications where petroleum-derived petrolatum compositions have historically been used. Representative examples of typical applications include personal care items (e.g., cosmetics, lip balms, lipsticks, perfumes, hand cleaners, hair dressings, ointments, sun care products, moisturizers, pharmaceutical ointments); plastics (e.g., a processing aid for PVC); food (e.g., cheese coatings, baking grease); telecommunications (e.g., cable filling or flooding compounds); industrial applications (e.g., grain dust suppressant, rust preventative coatings, adhesives, toilet boil rings, bone guard, and textile coatings).

Emulsions Comprising Petrolatum-Like Compositions

In some embodiments, the invention provides emulsions comprising hydrogenated metathesized unsaturated polyol esters. As used herein, the term "emulsion" refers to a stable dispersion of two or more immiscible liquids. In the emulsion, a first liquid (the "dispersed phase") is dispersed and held in suspension in the second liquid (the "continuous phase") with an emulsifier. Emulsions of the invention may be oil-in-water emulsions or water-in-oil emulsions. Oil-in-water emulsions have a dispersed phase comprising an organic material (e.g., an oily or waxy material) and a continuous phase comprising water. Water-in-oil emulsions have a dispersed phase comprising water and a continuous phase comprising an organic material (e.g., an oily or waxy material).

In some embodiments, oil-in-water emulsions of the invention comprise a dispersed phase comprising a hydrogenated metathesized unsaturated polyol ester. In other embodiments, the oil-in-water emulsions comprise a dispersed phase that comprises a mixture comprising: (i) a hydrogenated metathesized unsaturated polyol ester; and (ii) a polyol ester. In many embodiments, the dispersed phase comprises a material that has petrolatum-like properties. In other embodiments, the dispersed phase comprises a wax.

In some embodiments, the oil-in-water emulsions of the invention comprise about 60% wt. or less dispersed phase and about 40% wt. or greater continuous phase. In other embodiments, the oil-in-water emulsions of the invention comprise about 1% wt. to about 60% wt. dispersed phase and about 40% wt. to about 99% wt. continuous phase. In exemplary embodiments, the emulsions comprise about 1% wt. to about 30% wt. dispersed phase and about 70% wt. to about 99% wt. continuous phase.

In some embodiments, the dispersed phase of the emulsion has a particle size of about 1 μm or less. A small particle size promotes thorough, homogeneous incorporation with other ingredients that may be present in a formulation comprising the emulsion.

Suitable emulsifiers and surfactants include nonionic emulsifiers, ionic emulsifiers (e.g., anionic or cationic emulsifiers), and amphoteric emulsifiers. Nonionic emulsifers stabilize via a steric mechanism whereas ionic emulsifiers stabilize via an electrostatic mechanism. In some embodiments, a combination of two or more emulsifiers is used. For example, in some embodiments, anionic and nonionic emulsifiers are combined to provide increased stability to the emulsion.

Examples of nonionic surfactants include sorbitan esters such as sorbitan monolaurate, sorbitan monooleate, sorbitan monoisostearate; polyoxyethylene sorbitan esters such as polyoxyethylene sorbitan monoisostearate, polyoxyethylene sorbitan monolaurate, polyoxyethylene sorbitan monooleate; glycerol ethers such as glycerol monoisostearate, glycerol monomyristate; polyoxyethylene glycerol ethers such as polyoxyethylene glycerol monoisostearate, polyoxyethylene glycerol monomyristate; polyglycerin fatty acid esters such as diglyceryl monostearate, decaglyceryl decaisostearate, diglyceryl diisostearate; glycerin fatty acid esters such as glyceryl monocaprate, glyceryl monolaurate, glycerylmonomyristate, glycerylmonopalminate, glycerylmonooleate, glyceryl monostearate, glyceryl monolinoleate, glyceryl monoisostearate, glyceryl monodilinoleate, glyceryl monodicaprate; polyoxyethylene glycerin fatty acid esters such as polyoxyethylene glyceryl monomyristate, polyoxyethylene glyceryl monooleate, polyoxyethylene glyceryl monostearate; polyoxyethylene branched alkyl ethers such as polyoxyethylene octyldodecyl alcohol, polyoxyethylene-2-decyltetradecyl alcohol; polyoxyethylene alkyl ethers such as polyoxyethylene oleyl alcohol ether, polyoxyethylene cetyl alcohol ether; polyoxyethylene hydrogenated castor oil fatty acid esters such as polyoxyethylene hydrogenated castor oil, polyoxyethylene dihydrocholesterol ether, polyoxyethylene hydrogenated castor oil isostearate; polyoxyethylene alkyl aryl ethers such as polyoxyethylene octyl phenol ether. Representative examples of nonionic emulsifiers include ethoxylated cetaryl alcohol mixed with cetaryl alcohol (e.g., "PROMULGEN D" from Noveon, Cleveland Ohio) and glyceryl stearate (e.g., "ARLACEL 165" from Unichema Chemi BV, Netherlands).

Examples of anionic surfactants include salts of higher fatty acids such as oleic acid, stearic acid, isostearic acid, palmitic acid, myristic acid, behenic acid, for example, diethanolamine salts, triethanolamine salts, amino acid salts, potassium salts, sodium salts, ether carboxylic acid alkali salts, N-acylamino acid salts, N-acyl sarcosinates, higher alkyl sulfonates.

Examples of cationic or amphoteric surfactants include alkyl quaternary ammonium salts, polyamines and alkyl amine salts. Examples of colloidal emulsifiers include clay/lignosulfonates and clay/naphthalene sulfonates.

In some embodiments, the emulsion has a pH ranging from about 6 to 7, more typically ranging from about 6.0 to 6.5. Typically, the pH of the emulsion is adjusted to be within about 1 pH unit of a material that the emulsion is being added to. The pH of the emulsion may be adjusted, for example, by adding aqueous ammonia solution (i.e., to increase pH) or acetic acid (to reduce pH).

In some embodiments, water-in-oil emulsions of the invention comprise a continuous phase comprising a hydrogenated metathesized unsaturated polyol ester. For example, the continuous phase may comprise a mixture of: (i) a hydrogenated metathesized unsaturated polyol ester; and (ii) a polyol ester. The continuous phase may have petrolatum-like properties or may be a wax.

In many embodiments, the water-in-oil emulsions comprise from about 30 wt. % to about 70 wt. % continuous (i.e., oil) phase; about 20 wt. % to about 68 wt. % dispersed (i.e.,) phase; and about 2 wt. % to about 10 wt. % emulsifier. Representative examples of emulsifiers for water-in-oil emulsions include polyvalent soap emulsifiers combined with non-ionic PEG esters, silicone-based emulsifiers, and non-ionic emulsifiers.

Method of Manufacturing Emulsions:

Emulsions of the invention may be manufactured according to known methods in the art for manufacturing oil-in-water emulsions and water-in-oil emulsions. For oil-in-water emulsions, the water and emulsifier(s) are mixed until uniform. The mixture is then heated, for example, to about 80° C. and molten wax (e.g., hydrogenated metathesized unsaturated polyol ester) is added and mixed into the water/emulsifier phase until a uniform dispersion of the wax is formed. In many embodiments, a homogenizer or high shear mixer is used to reduce the particle size to a size where the emulsion is stable (e.g., about 0.1 to 1.5 microns). The emulsion may then be shock chilled to set the particles at the desired particle size.

Water-in-oil emulsions are typically prepared by a two-part process. The water phase and the oil phase are heated separately (e.g., about 70° C.-75° C. (about 5° to 10° C. about the melting point of the highest melting component in the formula)). The water phase and the oil phase are then mixed together. When the mixture is uniform, the mixture is slowly cooled to about 40° C. to 45° C. and other ingredients (e.g., fragrances, etc.) are added.

Applications of Emulsions:

Emulsions of the invention may be suitable in a wide variety of applications including, but not limited to, applications where petroleum-derived petrolatum or paraffin waxes have historically been used. Representative uses for the emulsions of the invention include in building materials (e.g., coatings for oriented strand board (OSB) or medium density fiberboard, lumber coatings); metal coatings (e.g., slip coating for cans, coil coatings); inks (e.g., additive to improve rub or scuff resistance in water based inks); fiberglass (e.g., antiblock or lubricant); molded latex articles (e.g., mold release for gloves or condoms); textiles (e.g., sizing agent or thread lubricant); floor finishes (e.g., additive to impart rub resistance); flexible films (e.g., processing aid); coatings (e.g., to add water repellency to deck stains or wood varnishes); polishes (e.g., hard surface, floor or auto polishes); and fruit/vegetable coatings (e.g., as a moisture barrier coating); cosmetic and personal care formulations (e.g., face, hand and body lotions/creams, lip care products, hair care products as a moisturizer or moisture barrier coating). Water-in-oil emulsions may be suitable for use, for example, in water-resistant sunscreens and in night creams.

The emulsions of the invention may be incorporated into formulations by simple mixing. The fine particle size provides thorough and homogeneous incorporation with other formulation ingredients.

The invention will now be described with reference to the following non-limiting examples.

EXAMPLES

Example 1

Example 1A Large Batch Metathesis Reaction

In a 50-gallon batch reactor, the soybean oil (87 Kg) was degassed overnight (~16 hrs) with argon or nitrogen at an estimated rate of 10 mL/min. Degassing the soybean oil yields optimal catalyst efficiencies and prevents metathesis catalyst decomposition The oil was then heated to 70° C. Ruthenium catalyst (C827, 4.2 g, 50 ppm) was added. The metathesis reaction was run for 2 hours, under an atmosphere of argon. The stir rate was not measured, but stirring was sufficient to cause a small amount of splash from the baffle. GC analysis of the corresponding methyl esters indicated 68% conversion. The metathesis catalyst was not removed prior to hydrogenation.

Metathesis Catalyst Removal Procedure

The metathesis catalyst was removed using THMP which was prepared by adding 245 g of tetrakishydroxymethyl phosphonium chloride (TKC) (1.03 mol, Cytec) and 500 mL of isopropyl alcohol (IPA) to a 2 L round-bottomed flask, degassing the mixture with nitrogen for 20 minutes, slowly adding 64 g (1.03 mol, 90% purity, Aldrich) of potassium hydroxide over 30 minutes to the vigorously stirring solution, while under a nitrogen atmosphere, and, after the potassium hydroxide has been added, stirring the reaction for an additional 30 minutes. The reaction was exothermic, and produced THMP, formaldehyde, potassium chloride, and water. The catalyst was then removed using the THMP by adding 25-100 mol equivalents of THMP per mole of ruthenium catalyst, stirring vigorously at 60-70° C. for 18 to 24 hours under nitrogen, adding degassed water or methanol (~150 mL/L of reaction mixture) and vigorously stirring for 10 minutes, and centrifuging the mixture for phase separation. This typically removes ruthenium to <1 ppm levels. The oil may have to be heated to remove the residual water or methanol. The aqueous phase will contain small amounts of IPA, formaldehyde, and potassium chloride, and will need to be purged or cleaned for recycling.

The second catalyst removal technique involves contacting the metathesis mixture with 5 wt % of Pure Flo 80 bleaching clay (i.e., 5 g bleaching clay/100 g metathesis mixture) for 4 hr at 70° C., followed by filtering the metathesis mixture through a plug of bleaching clay and sand. This technique typically removes ruthenium to <1 ppm levels.

Hydrogenation Procedure

The metathesis product can then be hydrogenated by heating the self-metathesized soybean oil to 350° F., while held under nitrogen, adding 0.4 wt % Ni catalyst to the oil once at 350° F., starting the flow of hydrogen at a pressure of 35 psi, having a hold temperature of about 410° F., and checking the reaction at 1 hour to see where the IV is in comparison to target. A 2.5 kg batch may take about 30-45 minutes. After about 2 hours (oil should be fully hydrogenated), nitrogen is put back in the vessel and the oil is cooled. The hydrogenated self-metathesized soybean oil may then be filtered to remove excess catalyst.

Example 2

Three sample metathesis products (A, C, and E) were subject to metathesis as described in EXAMPLE 1 to different degrees. These three metathesis products were hydrogenated, as described in EXAMPLE 1, to form hydrogenated versions of the metathesis products (B, D, and F).

Sample A was prepared starting with unrefined soybean oil (100 g) and 100 ppm of catalyst C627. The reaction was run at room temperature for 20 hrs and was then warmed to 40° C. for 5 hrs to yield 62% conversion, by GC analysis of the converted methyl ester. The metathesis catalyst was removed with THMP and water prior to hydrogenation.

Sample C was prepared starting with unrefined soybean oil (58 g) and 50 ppm of catalyst C627. The reaction was run at room temperature for 22 hrs, to yield 14% conversion. The metathesis catalyst was not removed before hydrogenation.

Sample E was prepared starting with unrefined soybean oil (68 g) and 50 ppm of catalyst C715. Catalyst C715 is the same as catalyst C627, except that it has bromine ligands where C627 has chlorine ligands. The self-metathesis reaction was run at room temperature for 22 hrs, to yield 27% conversion. The metathesis catalyst was removed with THMP and water prior to hydrogenation.

Polymer analysis indicated that each of the metathesized samples and their corresponding hydrogenated samples (in parentheses) A (B), C (D), and E (F) were reacted to different endpoints. As can be seen in TABLE 1, Sample C was the least reacted (i.e., the most triglyceride remained) and Sample A was the most reacted (i.e., lowest triglyceride and highest oligomer concentration). HPSEC analysis indicated Sample B had 21.2% unreacted triglyceride, Sample D had 93.3% unreacted triglyceride, and Sample F had 80.8% unreacted triglyceride. Samples A, C, and E had similar HPSEC chromatograms as their corresponding hydrogenated samples.

TABLE 1

|  | A | B | C | D | E | F |
|---|---|---|---|---|---|---|
| Total Oligomers | 75.6 | 78.7 | 6.9 | 6.7 | 20.5 | 19.3 |
| Tetramers and Higher Oligomers | 46.1 | 50.7 | ND | ND | 0.5 | 0.4 |
| Dimers | 16.4 | 16.1 | 6.5 | 6.4 | 16.5 | 15.9 |
| Trimers | 13.0 | 12.0 | 0.4 | 0.3 | 3.5 | 3.0 |
| TAG | 24.4 | 21.2 | 93.1 | 93.3 | 79.6 | 80.8 |

TABLE 2 shows the fatty acid composition of the six samples. The oil content is determined by converting the fatty acid methyl esters (FAME) into their triacylglycerol equivalents with the use of an internal standard, so the values are on a weight percent basis. All the individual fatty acids were determined by converting the FAME into fatty acid (FA) equivalents and are on a weight basis.

TABLE 2

|  | A | B | C | D | E | F |
|---|---|---|---|---|---|---|
| Trans (% w/w FA) | 13.35 | 1.36 | 8.02 | 0.01 | 11.49 | 1.65 |
| C18:1 (% w/w FA) | 8.06 | 1.87 | 20.13 | 0.11 | 17.86 | 2.21 |
| C18:2 (% w/w FA) | 8.81 | 0.58 | 41.64 | ND | 31.78 | 0.27 |
| C18:3 (% w/w FA) | 0.12 | 0.01 | 4.01 | ND | 2.26 | 0.01 |
| C18:0 (% w/w FA) | 4.03 | 18.51 | 4.11 | 68.12 | 4.06 | 50.38 |
| Saturated FA (% w/w FA) | 17.17 | 44.69 | 15.50 | 83.2 | 15.59 | 67.40 |
| C6:0 (% w/w FA) | 0.01 | 7.04 | ND | 1.90 | ND | 3.21 |

TABLE 2-continued

|  | A | B | C | D | E | F |
|---|---|---|---|---|---|---|
| C9:0 (% w/w) | ND | 3.95 | 0.01 | 1.05 | 0.01 | 1.77 |
| C12:0 (% w/w) | 0.02 | 1.17 | 0.01 | 0.29 | 0.02 | 0.50 |
| C15:0 (% w/w) | 0.04 | 10.70 | 0.03 | 2.73 | 0.03 | 4.55 |

Example 3

Preparation of Petrolatum Compositions

Petrolatum-like compositions suitable for use in cosmetics (e.g., as a replacement for petroleum-derived petrolatum) were prepared by blending the metathesis product B of Example 2 with 90 IV soybean oil in various ratios. TABLE 3 shows exemplary compositions.

TABLE 3

|  | Hydrogenated Metathesized Soybean Oil (parts) | 90 IV soybean oil (parts) | Melting Point ° F. (° C.) | Iodine Value of Blend |
|---|---|---|---|---|
| Blend 1 | 5 | 95 | 100.2 (37.9) | 85.7 |
| Blend 2 | 10 | 90 | 105.6 (40.9) | 81 |
| Blend 3 | 15 | 85 | 109.9 (43.3) | 76.1 |
| Blend 4 | 25 | 75 | 115.3 (46.3) | 64.1 |

Example 4

Emulsions

Ingredient List-Dispersed Phase

| INGREDIENT | DESCRIPTION |
|---|---|
| A | 100% HMSBO |
| B | 30% HMSBO in 300 Oil |
| C | 10% HMSBO in 300 Oil |
| D | 10% HMSBO/5% Glycerol in 300 Oil |
| E | 100% HSBO |
| F | PETROLATUM (Penreco Snow White Petrolatum) |

Ingredient List—Other Components

| NAME | FUNCTION | INCI DESIGNATION | SUPPLIER |
|---|---|---|---|
| CARBOPOL 980 (2% wt. solution) | THICKENER | CARBOMER | NOVEON |
| DISODIUM EDTA | CHELATOR | DISODIUM EDTA | CIBA |
| PROPYLENE GLYCOL | FREEZE/THAW STABILIZER | | |
| PROMULGEN D | HYDROPHOBID EMULSIFIER | CETEARYL ALCOHOL CETEARETH-20 | AMERCHOL |
| ARLACEL 165 | HYDROPHILLIC EMULSIFIER | GLYCERYL STEARATE PEG-100 STEARATE | UNIQEMA |
| SODIUM HYDROXIDE (20% wt. solution) | PH ADJUSTER | SODIUM HYDROXIDE | CHEMTECH |
| GERMABEN II | PARABEN PRESERVATIVE | PROPYLENE GLYCOL DIAZOLIDINYL UREA METHYLPARABEN PROPYLPARABEN | ISP SUTTON |
| WATER | | WATER | |

Emulsions 4-A to 4-E were prepared according to the following general procedure. The formulations are provided below.

(1) Phase A ingredients were combined together and were heated to 70° C. with mixing.

(2) Separately, phase B ingredients were combined and were heated to 70° C. while mixing. The phase B ingredients were mixed until the wax had melted and the phase B was uniform. Phase B ingredients were then added to the Phase A ingredients.

(3) Phase C was used to adjust the pH of batch to between 6.0 and 6.5.

(4) The batch was then cooled to 40° C. and phase D ingredients were added to the batch.

(5) The resulting emulsion was cooled to room temperature while being mixed.

Example Emulsion 4-A

| INGREDIENT | PHASE | % WT. | Batch Size |
|---|---|---|---|
| WATER | A | 62.75 | 313.75 |
| CARBOPOL 980 | A | 20.0 | 100.00 |
| DISODIUM EDTA | A | 0.10 | 0.50 |
| PROPYLENE GLYCOL | A | 2.0 | 10.00 |
| PROMULGEN D | B | 2.0 | 10.00 |
| DISPERSED OIL INGREDIENT 4-A | B | 10.0 | 50.00 |
| ARLACEL 165 | B | 1.5 | 7.50 |
| SODIUM HYDROXIDE | C | 0.65 | 3.25 |
| GERMABEN II | D | 1.0 | 5.00 |

Example 4-A Characteristics pH=6.23

Viscosity=50,000 cps (TC spindle @ 5 RPM)

Example Emulsion 4-B

| INGREDIENT | PHASE | % WT. | Batch Size |
|---|---|---|---|
| WATER | A | 62.75 | 313.75 |
| CARBOPOL 980 | A | 20.0 | 100.00 |
| DISODIUM EDTA | A | 0.10 | 0.50 |
| PROPYLENE GLYCOL | A | 2.0 | 10.00 |
| PROMULGEN D | B | 2.0 | 10.00 |
| DISPERSED OIL INGREDIENT 4-B | B | 10.0 | 50.00 |
| ARLACEL 165 | B | 1.5 | 7.50 |
| SODIUM HYDROXIDE | C | 0.65 | 3.25 |
| GERMABEN II | D | 1.0 | 5.00 |

Example 4-B Characteristics pH=6.01
Viscosity=46,000 cps (TC spindle @ 5 RPM)

Example Emulsion 4-C

| INGREDIENT | PHASE | % WT. | Batch Size |
|---|---|---|---|
| WATER | A | 62.75 | 313.75 |
| CARBOPOL 980 | A | 20.0 | 100.00 |
| DISODIUM EDTA | A | 0.10 | 0.50 |
| PROPYLENE GLYCOL | A | 2.0 | 10.00 |
| PROMULGEN D | B | 2.0 | 10.00 |
| DISPERSED OIL INGREDIENT 4-C | B | 10.0 | 50.00 |
| ARLACEL 165 | B | 1.5 | 7.50 |
| SODIUM HYDROXIDE | C | 0.65 | 3.25 |
| GERMABEN II | D | 1.0 | 5.00 |

Example 4-C Characteristics pH=6.14
Viscosity=66,000 cps (TC spindle @ 5 RPM)

Example Emulsion 4-D

| INGREDIENT | PHASE | % WT. | Batch Size |
|---|---|---|---|
| WATER | A | 62.8 | 314.00 |
| CARBOPOL 980 | A | 20.0 | 100.00 |
| DISODIUM EDTA | A | 0.10 | 0.50 |
| PROPYLENE GLYCOL | A | 2.0 | 10.00 |
| PROMULGEN D | B | 2.0 | 10.00 |
| DISPERSED OIL INGREDIENT 4-D | B | 10.0 | 50.00 |
| ARLACEL 165 | B | 1.5 | 7.50 |
| SODIUM HYDROXIDE | C | 0.60 | 3.00 |
| GERMABEN II | D | 1.0 | 5.00 |

Example 4-D Characteristics pH=5.93
Viscosity=58,000 cps (TC spindle @ 5 RPM)

Example Emulsion 4-E

| INGREDIENT | PHASE | % WT. | Batch Size |
|---|---|---|---|
| WATER | A | 62.75 | 313.75 |
| CARBOPOL 980 | A | 20.0 | 100.00 |
| DISODIUM EDTA | A | 0.10 | 0.50 |
| PROPYLENE GLYCOL | A | 2.0 | 10.00 |
| PROMULGEN D | B | 2.0 | 10.00 |
| DISPERSED OIL INGREDIENT 4-E | B | 10.0 | 50.00 |
| ARLACEL 165 | B | 1.5 | 7.50 |
| SODIUM HYDROXIDE | C | 0.65 | 3.25 |
| GERMABEN II | D | 1.0 | 5.00 |

Example 4-E Characteristics pH=6.37
Viscosity=40,400 cps (TB spindle @5 rpm)

Example EMULSION 4-F (CONTROL)

| INGREDIENT | PHASE | % WT. | BATCH SIZE |
|---|---|---|---|
| WATER | A | 63.05 | 315.25 |
| CARBOPOL 980 | A | 20.0 | 100.00 |
| DISODIUM EDTA | A | 0.10 | 0.50 |
| PROPYLENE GLYCOL | A | 2.00 | 10.00 |
| PROMULGEN D | B | 2.00 | 10.00 |
| DISPERSED OIL INGREDIENT 4-F | B | 10.0 | 50.00 |
| ARLACEL 165 | B | 1.50 | 7.50 |
| SODIUM HYDROXIDE | C | 0.35 | 1.75 |
| GERMABEN II | D | 1.0 | 5.00 |

Example 4-F Characteristics pH=6.34
Viscosity=36,000 cps (TB spindle @ 5 rpm)
Emulsion Stability Study

TABLE 4

| | Example No. | | | | | |
|---|---|---|---|---|---|---|
| | 4-A | 4-B | 4-C | 4-D | 4-E | 4-F |
| Dispersed Phase | A | B | C | D | E | F |
| Preparation Day | Day 12 | Day 8 | Day 5 | Day 1 | Day 28 | Day 35 |
| Room Temp[3] | Stable | Stable | Stable | Stable | Stable | Stable |
| 3 Freeze-Thaw Cycles[1] | Stable | Stable | Stable | Stable | Stable | Stable |
| Oven[2] | Stable | Stable | Stable | Stable | Stable | Stable |

[1]During each cycle the sample was frozen at −5° C. for 24 hours followed by being thawed at room temperature for 24 hours.
[2]Oven temperature was 45° C.
[3]Stability was tested on Days 28, 35, 44, and 57
Observations:
Day 28 - all samples in oven and room temperature appeared the same. Samples have not changed in color or odor.
Day 35 - all samples in the oven and room temperature looked very stable except Example 4-E which appeared the same but had become gelatinous after 3 days at 45° C.
Day 44 - all samples in the oven and room temperature were stable in color and odor. Example 4-E became gelatinous at room temperature.

The emulsion compositions 4-A to 4-F were evaluated for use as hand creams. The results are presented in TABLE 5.

TABLE 5

| Emulsion No. | Appearance, Peak behavior | Odor | Initial application: rub-in, tack (stickiness) | Length of "play time" | Observations of skin after application |
|---|---|---|---|---|---|
| 4-A | Grainy emulsion | Very strong anisette smell | Tacky and waxy feel | Very short play time | A lot of drag but not like petrolatum: a dry drag, not greasy, but unpleasant |
| 4-B | Nice white silky cream | Fragrant odor; like anisette. | Nice emollient feel, No noticeable tack, little whitening effect | Short play time | Some drag but disappears and leaves skin smooth feeling. Heavier (residual) feel than 4-C, doesn't impart shine |
| 4-C | Nice white silky cream | Slight anisette odor | Light non-oily feel, watery, no tack | Good play time | Disappears, no residual feel, no drag, silky feel, good cascade effect |
| 4-D | Nice white silky cream | Light anisette odor | Liquefies on finger on pick up; whitening effect; minor tack | Good play time | Smooth, not heavy, nice feel |
| 4-E | Noticeably more satin/whipped cream than silky | Little odor | Heavy feel, whitening effect | Rubs in quickly | Heavy feel, quickly becomes significant drag, unpleasant waxy feel with flaking |
| 4-F | Grainy (fine-grained); good peak | Very Slight Odor (just what is present from emulsifiers) | Rub in gives heavy feel with lots of tack, doesn't change much over rub | Very slow to rub in | Thicker film and slow dry down gives greasy, heavy feel lots of drag |

Example 5

Test Procedure

The efficacy of topical formulations in recovery of skin barrier was evaluated. The protocol involved test sites on the volar surface of the forearm. Each test material was tested on at least 25 subjects. All subjects had an untreated site. Each test site was 5 cm wide×5 cm long. TEWL readings were taken at each site. The sites were then damaged by tape stripping (using Blenderm™ surgical tape (from 3M Company)) until TEWL readings were at least 20 mg/m²/h. Just prior to product application, baseline TEWL readings were taken. Baseline Skicon and Corneometer readings were also taken at this time. TEWL was measured with a Dermalab Evaporimeter (Cortex Technology, Denmark). Skin hydration was assessed by conductance measurement with the Skicon-200 (I.B.S., Japan) and MT8C probe (Measurement Technologies, Cincinnati, Ohio) and by capacitance measurement with a Corneometer 820 (Courage+Khazaka, Germany). Test material was applied at a dose of 2 µl/cm² (50 µl) or 2 µg/cm² (0.05 g) as appropriate to the site. Subject had a minimum of 30 minutes acclimation prior to any instrument readings. Subjects were in a climate-controlled room. TEWL readings were taken 30 minutes, 1-hour and 4-hours post application. Final Skicon and Corneometer readings were taken at 4-hours post application.
Formulations Tested:
Petrolatum-Like Compositions:

Example 5-1

2% Wt. Vegetable Wax; 8% Wt. HMSBO, and 90% Wt. SBO

Example 5-2

6% Wt. Vegetable Wax, 26% Wt. HMSBO, and 71% Wt. SBO

Petrolatum: Crompton White Fonoline USP Petrolatum
Soybean Oil: Cargill refined, bleached, and deodorized soybean oil
Mineral Oil: Mineral Oil USP (Heavy)
CORNEOMETER TESTING: After four hours of treatment following skin damage, EXAMPLE 5-1 provided significant increase in skin moisture content from baseline, enhanced moisture relative to untreated skin, and exhibited results similar to a commercial petrolatum. The skin feel with EXAMPLE 5-1 was non-greasy. The Corneometer results are reported in TABLE 6.

TABLE 6

| SAMPLE | 4 hour Corneometer (Mean Change from Baseline) |
|---|---|
| EXAMPLE 5-1 | 8.52 |
| Petrolatum | 8.50 |
| Untreated | 5.81 |

SKICON TESTING: EXAMPLE 5-1 provided a significant increase in skin hydration from the baseline, enhanced hydration relative to untreated skin, and exhibited better hydration than soybean oil. The Skicon results are reported in TABLE 7.

Ingredient List:
62A: HMSBO (hydrogenated self-metathesized soybean oil)
62D: 20% HMSBO in 300 oil (300 oil is partially hydrogenated, cooled, filtered soybean oil)
62E: 33% HMSBO/67% hydrogenated soybean oil
91A: MSBO (self-metathesized soybean oil)

TABLE 9

| INGREDIENTS | 9-1 | 9-2 | 9-3 | 9-4 | 9-5 | 9-6 | 9-7 | 9-8 |
|---|---|---|---|---|---|---|---|---|
| White Beeswax | 8.00 | 8.00 | 8.00 | 8.00 | 8.00 | 8.00 | 0.00 | 8.00 |
| Candelilla Wax Regular | 5.00 | 5.00 | 5.00 | 0.00 | 0.00 | 5.00 | 5.00 | 0.00 |
| Carnauba Wax #1 | 6.00 | 6.00 | 6.00 | 0.00 | 0.00 | 6.00 | 6.00 | 0.00 |
| Softisan 649 | 7.50 | 7.50 | 7.50 | 7.50 | 7.50 | 7.50 | 7.50 | 7.50 |
| Uvinul MC 80 | 3.25 | 3.25 | 3.25 | 3.25 | 3.25 | 3.25 | 3.25 | 3.25 |
| Liponate GC | 10.00 | 10.00 | 10.00 | 10.00 | 10.00 | 10.00 | 10.00 | 10.00 |
| Lanolin Oil | 0.00 | 0.00 | 0.00 | 10.00 | 10.00 | 0.00 | 10.00 | 10.00 |
| Naturechem GTR | 4.50 | 4.50 | 4.50 | 4.50 | 4.50 | 4.50 | 4.50 | 4.50 |
| Floraesters 15 | 5.00 | 5.00 | 5.00 | 5.00 | 5.00 | 5.00 | 5.00 | 5.00 |
| Jarchol I20 | 5.00 | 5.00 | 5.00 | 5.00 | 5.00 | 5.00 | 5.00 | 5.00 |
| *Macadamia* Nut Oil | 2.50 | 2.50 | 2.50 | 2.50 | 2.50 | 2.50 | 2.50 | 2.50 |
| Propyl Paraben | 0.20 | 0.20 | 0.20 | 0.20 | 0.20 | 0.20 | 0.20 | 0.20 |
| BHT | 0.05 | 0.05 | 0.05 | 0.05 | 0.05 | 0.05 | 0.05 | 0.05 |
| Lipovol CO | 33.00 | 33.00 | 33.00 | 22.00 | 22.00 | 0.00 | 15.00 | 22.00 |
| 62A | 0.00 | 10.00 | 0.00 | 22.00 | 0.00 | 0.00 | 26.00 | 0.00 |
| 62D | 0.00 | 0.00 | 10.00 | 0.00 | 0.00 | 0.00 | 0.00 | 0.00 |
| 62E | 0.00 | 0.00 | 0.00 | 0.00 | 0.00 | 0.00 | 0.00 | 22.00 |
| 91A | 10.00 | 0.00 | 0.00 | 0.00 | 0.00 | 43.00 | 0.00 | 0.00 |
| Soy Wax | 0.00 | 0.00 | 0.00 | 0.00 | 22.00 | 0.00 | 0.00 | 0.00 |
| OBSERVATIONS | GOOD | TOO HARD | GOOD | TOO SOFT | TOO HARD | GOOD | TOO HARD | GOOD |

TABLE 7

| SAMPLE | 4 hour Skicon (Mean Change from Baseline) |
|---|---|
| EXAMPLE 5-1 | 148.77 |
| Petrolatum | 394.85 |
| Untreated | 99.22 |
| Soybean Oil | 83.66 |

TEWL TESTING: EXAMPLE 5-2 provided a significant decrease in moisture loss from baseline, exhibited better TEWL properties than untreated and soybean oil, and can be a natural-based alternative to mineral oil for TEWL benefits. The TEWL results are reported in TABLE 8.

TABLE 8

| SAMPLE | 4 hour TEWL (Mean Change from Baseline) |
|---|---|
| EXAMPLE 5-2 | −13.74 |
| Petrolatum | −18.12 |
| Untreated | −5.78 |
| Soybean Oil | −8.76 |
| Mineral Oil | −12.80 |

EXAMPLES 5-1 and 5-2 provided significant hydration properties to skin from baseline, enhanced moisture level relative to untreated skin, provided significant improvement in skin barrier resulting in benefits in formulations preventing barrier disruption.

Example 6

Lipsticks were formulated using certain petrolatum-like compositions of the invention. The lipstick formulations are provided in TABLE 9.

The above results demonstrate that metathesized soybean oil and hydrogenated metathesized soybean oil can replace several common ingredients utilized in the formulating of lipsticks such as lanolin, carnauba wax, candelilla wax, and castor oil. Hydrogenated soybean oil alone (soy wax) cannot achieve this.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A composition comprising: an emulsion comprising a dispersed phase that comprises a hydrogenated metathesized unsaturated polyol ester and a polyol ester,
    wherein the dispersed phase has an iodine value of 20 to 100; and
    wherein the dispersed phase has a viscosity at 210° F. of about 100 SUS or less and a cone penetration at 77° F. (25° C.) of about 100 dmm to about 300 dmm, wherein the hydrogenated metathesized unsaturated polyol ester is hydrogenated metathesized unsaturated soybean oil and wherein the polyol ester is soybean oil.
2. The composition of claim 1, wherein the composition is an oil-in-water emulsion or a water-in-oil emulsion.
3. The composition of claim 1, wherein the composition is an oil-in-water emulsion and further comprises an emulsifier.

4. The composition of claim 1, wherein at least a portion of the soybean oil is partially hydrogenated.

5. The composition of claim 1, wherein the dispersed phase comprises about 50% wt. or less hydrogenated metathesized unsaturated polyol ester.

6. The composition of claim 1, wherein the dispersed phase comprises about 5% wt. to about 25% wt. hydrogenated metathesized unsaturated polyol ester.

7. The composition of claim 1, wherein the dispersed phase comprises about 5% wt. to about 25% wt. hydrogenated metathesized unsaturated polyol ester and about 75% wt. to about 95% wt. polyol ester.

8. The composition of claim 1, wherein the hydrogenated metathesized unsaturated polyol ester has an iodine value of about 100 or less.

9. The composition of claim 1, wherein the hydrogenated metathesized unsaturated polyol ester has an iodine value of about 100 or less and the polyol ester has an iodine value of about 80 to 120.

10. The composition of claim 3, wherein the emulsion has a viscosity ranging from about 20,000 cps to 80,000 cps.

11. The composition of claim 3, wherein the dispersed phase has a congealing point of about 100° F. to about 140° F. (37.8° C. to 60.0° C.).

12. The composition of claim 3, wherein the dispersed phase has a drop melt point of about 100° F. to about 150° F. (37.8° C. to 65.6° C.).

13. The composition of claim 3, wherein the dispersed phase comprises about 1% wt. to about 60% wt. and the continuous phase comprises about 40% wt. to about 99% wt. of the composition.

14. The composition of claim 3, wherein the emulsifier is selected from the group consisting of nonionic emulsifiers, anionic emulsifiers, cationic emulsifiers, amphoteric emulsifiers, and mixtures thereof.

15. A personal care item comprising the emulsion of claim 1.

* * * * *